United States Patent
LaBelle et al.

(10) Patent No.: US 11,346,798 B2
(45) Date of Patent: May 31, 2022

(54) METHODS AND DEVICE FOR TUNING MULTIPLEXED MARKERS FOR DISEASE ASSAY

(75) Inventors: Jeffrey LaBelle, Tempe, AZ (US); Ugur Demirok, Beaverton, OR (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1340 days.

(21) Appl. No.: 13/809,387

(22) PCT Filed: Jul. 12, 2011

(86) PCT No.: PCT/US2011/043652
§ 371 (c)(1),
(2), (4) Date: Mar. 29, 2013

(87) PCT Pub. No.: WO2012/009322
PCT Pub. Date: Jan. 19, 2012

(65) Prior Publication Data
US 2013/0183243 A1    Jul. 18, 2013

Related U.S. Application Data

(60) Provisional application No. 61/363,394, filed on Jul. 12, 2010.

(51) Int. Cl.
| | |
|---|---|
| *G01N 27/02* | (2006.01) |
| *G01N 33/543* | (2006.01) |
| *G01N 27/327* | (2006.01) |
| *A61B 5/0205* | (2006.01) |
| *G01N 33/68* | (2006.01) |

(52) U.S. Cl.
CPC ......... *G01N 27/026* (2013.01); *A61B 5/0205* (2013.01); *G01N 27/3278* (2013.01); *G01N 33/5438* (2013.01); *G01N 33/6869* (2013.01)

(58) Field of Classification Search
CPC .......... G01N 33/5438; G01N 27/3278; G01N 27/026; G01N 33/6869; G01N 33/54346; A61B 5/0205
See application file for complete search history.

(56) References Cited

U.S. PATENT DOCUMENTS

| | | | |
|---|---|---|---|
| 5,234,566 A | 8/1993 | Osman et al. | |
| 6,846,639 B2 | 1/2005 | Miles | |
| 7,112,816 B2 | 9/2006 | Schlaf et al. | |
| 8,753,874 B2 * | 6/2014 | Gumbrecht | C12M 1/34 435/287.2 |
| 8,815,178 B2 | 8/2014 | Bishop | |
| 9,532,747 B2 | 1/2017 | LaBelle | |
| 9,909,942 B2 | 3/2018 | LaBelle | |
| 10,386,321 B2 | 8/2019 | LaBelle | |
| 10,724,066 B2 | 7/2020 | LaBelle et al. | |
| 10,939,857 B2 | 3/2021 | LaBelle et al. | |
| 10,948,366 B2 | 3/2021 | LaBelle et al. | |
| 10,983,017 B2 | 4/2021 | LaBelle et al. | |
| 2002/0137032 A1 | 9/2002 | Hefti | |
| 2003/0036054 A1 | 2/2003 | Ladisch et al. | |
| 2004/0157263 A1* | 8/2004 | Diessel | G01N 33/5438 435/7.1 |
| 2005/0003560 A1 | 1/2005 | Zeng et al. | |
| 2008/0124776 A1 | 5/2008 | Wei | |
| 2008/0185295 A1 | 8/2008 | Briman et al. | |
| 2009/0082691 A1 | 3/2009 | Denison et al. | |
| 2009/0092965 A1 | 4/2009 | Weiss et al. | |
| 2009/0117571 A1* | 5/2009 | Solanki | G01N 33/5438 435/6.11 |
| 2009/0117589 A1 | 5/2009 | Southern | |
| 2010/0203516 A1* | 8/2010 | Campbell | C12Q 1/6816 435/6.11 |
| 2012/0244630 A1* | 9/2012 | Svendsen | G01N 33/54313 436/501 |
| 2015/0057513 A1 | 2/2015 | LaBelle | |
| 2019/0150815 A1 | 5/2019 | LaBelle | |
| 2019/0369042 A1 | 12/2019 | LaBelle | |
| 2020/0011778 A1 | 1/2020 | Honikel | |

(Continued)

FOREIGN PATENT DOCUMENTS

| | | |
|---|---|---|
| WO | 2007104058 A2 | 9/2007 |
| WO | 2008045799 A2 | 4/2008 |

(Continued)

OTHER PUBLICATIONS

Hansen et al., JACS, 2006, 128, 2228-9. (Year: 2006).*
Wu et al., Analytical Chemistry, 2008, 80, p. 6072-6077. (Year: 2008).*
Amur, S. et al., "Integration and use of biomarkers in drug development, regulation and clinical practice: a US regulatory perspective", Biomarkers in Medicine, Jun. 2008, vol. 2, No. 3, pp. 305-311 DOI:10.2217/17520363.2.3.305.
Anker, J. et al., "Biosensing with plasmonic nanosensors", Nature Materials, Jun. 2008, vol. 7, pp. 442-453 DOI:10.1038/nmat2162.

(Continued)

*Primary Examiner* — Michael G. Hartley
*Assistant Examiner* — Leah H Schlientz
(74) *Attorney, Agent, or Firm* — Quarles & Brady LLP

(57) ABSTRACT

The present invention relates to a diagnostic device and methods of using the same for diagnostic assays for monitoring the presence of biological samples wherein the device allows for the determination of at least two assay components on one sensor. More specifically, the invention relates to a multi-marker electrochemical impedance spectroscopy sensor comprising a plurality of molecular recognition elements wherein the sensor comprises multiple different molecular recognition element types that are tuned in a manner that alters the frequency of the molecular recognition element type such that it is at a detectably different frequency to the frequency of other molecular recognition element types on the same sensor.

13 Claims, 16 Drawing Sheets

(56) References Cited

U.S. PATENT DOCUMENTS

| | | |
|---|---|---|
| 2020/0064297 A1 | 2/2020 | Probst et al. |
| 2020/0354764 A1 | 11/2020 | La Belle et al. |
| 2021/0063334 A1 | 3/2021 | LaBelle et al. |

FOREIGN PATENT DOCUMENTS

| | | |
|---|---|---|
| WO | 2009032901 A1 | 3/2009 |
| WO | 2010111484 A1 | 9/2010 |

OTHER PUBLICATIONS

Bailon, R. et al., "Continuous Subcutaneous Insulin Infusion (Insulin Pump) Therapy can be Safely Used in the Hospital in Select Patients", Endocrine Practice, Jan. 2009, vol. 15, No. 1, pp. 24-29 DOI:10.4158/EP.15.1.24.

Bailon, R. et al., "Temporal and Geographic Patterns of Hypoglycemia among Hospitalized Patients with Diabetes Mellitus", Journal of Diabetes Science and Technology, Mar. 2009, vol. 3, No. 2, pp. 261-268 DOI:10.1177/193229680900300206.

Bard, A. J., et al. "Techniques based on Concepts of Impedance." Electrochemical Methods 2.482 (2001): 368-416.

Bersoux, S. et al., "An Outpatient-Based Clinical Program for Type 2 Diabetes Prevention", Endocrine Practice, Jan. 2010, vol. 16, No. 1, pp. 21-29 DOI:10.4158/EP09151.OR.

Bersoux, S. et al., "Hemoglobin A1c Testing Alone Does Not Sufficiently Identify Patients With Prediabetes", American Journal of Clinical Pathology, May 2011, vol. 135, No. 5, pp. 674-677 DOI:10.1309/AJCPJBG0WYRAHN0R.

Bhavsar, K. et al., "A cytokine immunosensor for Multiple Sclerosis detection based upon label-free electrochemical impedance spectroscopy using electroplated printed circuit board electrodes", Biosensors and Bioelectronics, Oct. 2009, vol. 25, No. 2, pp. 506-509 DOI:10.1016/j.bios.2009.07.017.

Bishop, D. et al., "A Disposable Tear Glucose Biosensor—Part 1: Design and Concept Testing", Journal of Diabetes Science and Technology, Mar. 2010, vol. 4, No. 2, pp. 299-306 DOI:10.1177/193229681000400209.

Brockhausen, I. et al., "Mucin-type O-glycans in human colon and breast cancer: glycodynamics and functions", EMBO Reports, Jun. 2006, vol. 7, No. 6, pp. 599-604 DOI:10.1038/sj.embor.7400705.

Brust, M. et al., "Self-Assembled Gold Nanoparticle Thin Films with Nonmetallic Optical and Electronic Properties", Langmuir, Sep. 1998, vol. 14, No. 19, pp. 5425-5429 DOI:10.1021/la980557g.

Cai, J. et al., "Flexible thick-film electrochemical sensors: Impact of mechanical bending and stress on the electrochemical behavior", Sensors and Actuators B: Chemical, Mar. 2009 (available online Nov. 2008), vol. 137, No. 1, pp. 379-385 DOI:10.1016/j.snb.2008.10.027.

Chaki, N. et al., "Effect of Chain Length and the Nature of the Monolayer on the Electrical Behavior of Hydrophobically Organized Gold Clusters", The Journal of Physical Chemistry B, Dec. 2003, vol. 107, No. 49, pp. 13567-13574 DOI:10.1021/jp035032y.

Chakkera, H. et al., "Hyperglycemia during the Immediate Period after Kidney Transplantation", Clinical Journal of the American Society of Nephrology, Apr. 2009, vol. 4, No. 4, pp. 853-859 DOI:10.2215/CJN.05471008.

Chakkera, H. et al., "Relationship between Inpatient Hyperglycemia and Insulin Treatment after Kidney Transplantation and Future New Onset Diabetes Mellitus", Clinical Journal of the American Society of Nephrology, Sep. 2010, vol. 5, No. 9, pp. 1669-1675 DOI:10.2215/CJN.09481209.

Cheekati, V. et al., "Insulin therapy for inpatients with diabetes: Perceptions of resident physicians from disparate geographic training programs", Insulin, Apr. 2009, vol. 4, No. 2, pp. 106-113 DOI:10.1016/S1557-0843(09)80019-5.

Cheekati, V. et al., "Perceptions of Resident Physicians AboutManagement of Inpatient Hyperglycemia in anUrban Hospital", Journal of Hospital Medicine, Jan. 2009, vol. 4, No. 1, pp. E1-E8 DOI:10.1002/jhm.383.

Chen, H. et al., "An electrochemical impedance immunosensor with signal amplification based on Au-colloid labeled antibody complex", Sensors and Actuators B: Chemical, Sep. 2006 (available online Dec. 2005), vol. 117, No. 1, pp. 211-218 DOI:10.1016/j.snb.2005.11.026.

Chen, L. et al., "Sensitive detection of Epstein-Barr virus-derived latent membrane protein 1 based on CdTe quantum dots-capped silica nanoparticle labels", Clinica Chimica Acta, Dec. 2010 [available online Aug. 2010], vol. 411, No. 23-24, pp. 1969-1975 DOI:10.1016/j.cca.2010.08.012.

Chou, P. et al., "Prediction of protein conformation", Biochemistry, Jan. 1974, vol. 13, No. 2, pp. 222-245 DOI:10.1021/bi00699a002.

Chumbimuni-Torres, K. et al., "Amplified potentiometric transduction of DNA hybridization using ion-loaded liposomes", Analyst, May 2010, vol. 135, pp. 1618-1623 DOI:10.1039/C0AN00198H.

Cook, C. et al., "Beliefs About Hospital Diabetes and Perceived Barriers to Glucose Management Among Inpatient Midlevel Practitioners", The Science of Diabetes Self-Management and Care, Jan. 2008, vol. 34, No. 1, pp. 75-83 DOI:10.1177/0145721707311957.

Cook, C. et al., "Development of Computer-Based Training to Enhance Resident Physician Management of Inpatient Diabetes", Journal of Diabetes Science and Technology, Nov. 2009, vol. 3, No. 6, pp. 1377-1387 DOI:10.1177/193229680900300618.

Cook, C. et al., "Diabetes and Hyperglycemia Quality Improvement Efforts in Hospitals in the United States: Current Status, Practice Variation, and Barriers to Implementation", Endocrine Practice, Mar. 2010, vol. 16, No. 2, pp. 219-230 DOI:10.4158/EP09234.OR.

Cook, C. et al., "Inpatient glucose control: a glycemic survey of 126 U.S. hospitals", Journal of Hospital Medicine, Dec. 2009, vol. 4, No. 9, pp. E7-E14 DOI:10.1002/jhm.533.

Cook, C. et al., "Inpatient to Outpatient Transfer of Diabetes Care: Planning for an Effective Hospital Discharge", Endocrine Practice, Apr. 2009, vol. 15, No. 3, pp. 263-269 DOI:10.4158/EP.15.3.263.

Cook, C. et al., "Understanding and Improving Management of Inpatient Diabetes Mellitus: The Mayo Clinic Arizona Experience", Journal of Diabetes Science and Technology, Nov. 2008, vol. 2, No. 6, pp. 925-931 DOI:10.1177/193229680800200602.

Dai, Z. et al., "Nanoparticle-Based Sensing of Glycan-Lectin Interactions", Journal of the American Chemical Society, Aug. 2006, vol. 128, No. 31, pp. 10018-10019 DOI:10.1021/ja063565p.

Datar, R. et al., "Cantilever Sensors: Nanomechanical Tools for Diagnostics", MRS Bulletin, Jun. 2009, vol. 34, pp. 449-454 DOI:10.1557/mrs2009.121.

Demirok, U.K., et al. "The development of a label-free electrochemical impedance based point-of-care technology for multimarker detection." J Biosens Bioelectron (2013): 1-7.

Diamandis, E. et al., "Prostate specific antigen—a new constituent of breast cyst fluid", Breast Cancer Research and Treatment, Oct. 1996, vol. 38, No. 3, pp. 259-264 DOI:10.1007/BF01806144.

Dube, D. et al., "Glycans in cancer and inflammation—potential for therapeutics and diagnostics", Nature Reviews Drug Discovery, Jun. 2005, vol. 4, No. 6, pp. 477-488 DOI:10.1038/nrd1751.

Fairchild, A. B., et al. "A label-free, rapid multimarker protein impedance-based immunosensor." 2009 ICME International Conference on Complex Medical Engineering. IEEE, 2009.

Garnier, J. et al., "GOR method for predicting protein secondary structure from amino acid sequence", Methods in Enzymology, 1996, vol. 266, pp. 540-553 DOI:10.1016/S0076-6879(96)66034-0.

Greijer, A. et al., "Multiplex real-time NASBA for monitoring expression dynamics of human cytomegalovirus encoded IE1 and pp67 RNA", Journal of Clinical Virology, Feb. 2002 (available online Dec. 2001), vol. 24, No. 1-2, pp. 57-66 DOI:10.1016/S1386-6532(01)00227-X.

Harrell, F., "Multivariable Modeling Strategies", Regression Modeling Strategies, 2001, pp. 61 DOI:10.1007/978-1-4757-3462-1_4.

Heinemann, L., "Finger Pricking and Pain: A Never Ending Story", Journal of Diabetes Science and Technology, Sep. 2008, vol. 2, No. 5, pp. 919-921 DOI:10.1177/193229680800200526.

HQINC, "Recognize Elevated Core Body Temperature" [online], NQINC, retrieved on May 17, 2010 from archive.org, as it appeared on Apr. 17, 2010], retrieved from the internet: https://web.archive.org/web/20100417061056/https://www.hqinc.net/.

(56) References Cited

OTHER PUBLICATIONS

International Searching Authority. Written Opinion for application PCT/US2011/043652, dated Oct. 31, 2011. 7 pages.
Kidd, M. et al., "Feminizing Adrenal Neoplasms: Case Presentations and Review of the Literature", Journal of Clinical Oneology, Feb. 2011, vol. 29, No. 6, pp. e127-e130 DOI:10.1200/JCO.2010. 31.4799.
Kolberg, J. et al., "Development of a Type 2 Diabetes Risk Model From a Panel of Serum Biomarkers From the Inter99 Cohort", Diabetes Care, Jul. 2009, vol. 32, No. 7, pp. 1207-1212 DOI:10. 2337/dc08-1935.
Kumar, S. et al., "AutoSense: Wireless Skin Patch Sensors to Detect and Transmit Addiction and Psychosocial Stress Data" [online], NIH, retrieved on May 17, 2010 from archive.org, as it appeared on May 27, 2010], retrieved from the internet: https://web.archive.org/web/20100527090629/http://www.gei.nih.gov/exposurebiology/program/docs/SantoshKumar.pdf.
La Belle, J. "The Iterative Design Steps of a Noninvasive Tear TOUCH Glucose Sensor" Presented at the 2010 SMTA/MEPTEC Medical Electronics Symposium. Sep. 22-23, 2010 at Arizona State University in Tempe, AZ. 44 pages.
La Belle, J. et al., "A Disposable Tear Glucose Biosensor—Part 2: System Integration and Model Validation", Journal of Diabetes Science and Technology, Mar. 2010, vol. 4, No. 2, pp. 307-311 DOI:10.1177/193229681000400210.
La Belle, J. et al., "Design and Optimization of a Disposable, Noninvasive Tear-Glucose Sensor", Ninth Annual Diabetes Technology Meeting (Nov. 5-7, 2009, Burlingame, California), 2009, p. A79.
La Belle, J. et al., "Design Improvements of a Disposable, Noninvasive Tear-Glucose Sensor", Tenth Annual Diabetes Technology Meeting (Nov. 11-13, 2010, Bethesda, Maryland), 2010, p. A75.
La Belle, J. et al., "Development of a novel single sensor multiplexed marker assay", Analyst, Feb. 2011, vol. 136, No. 7, pp. 1496-1501 DOI:10.1039/C0AN00923G.
La Belle, J. et al., "Label-Free and Ultra-Low Level Detection of *Salmonella enterica* Serovar Typhimurium Using Electrochemical Impedance Spectroscopy", Electroanalysis, Oct. 2009, vol. 21, No. 20, pp. 2267-2271 DOI:10.1002/elan.200904666.
La Belle, J. et al., "Label-Free Impedimetric Detection of Glycan-Lectin Interactions", Analytical Chemistry, Sep. 2007, vol. 79, No. 18, pp. 6959-6964 DOI:10.1021/ac070651e.
La Belle, J. et al. 2007. A Cytokine Immunosensor Based Upon Label-Free Electrochemical Impedance Spectroscopy. Biosens. Bioelec. 23, 428-31.
International Search Report dated Oct. 31, 2011 for PCT/US2011/043652.
Laxman, B. et al., "A First-Generation Multiplex Biomarker Analysis of Urine for the Eady Detection of Prostate Cancer", Cancer Research, Feb. 2008, vol. 68, No. 3, pp. 645-649 DOI:10.1158/0008-5472.CAN-07-3224.
Leonhardi, B. et al., "Use of Continuous Subcutaneous Insulin Infusion (Insulin Pump) Therapy in the Hospital: A Review of One Institution's Experience", Journal of Diabetes Science and Technology, Nov. 2008, vol. 2, No. 6, pp. 948-962 DOI:10.1177/193229680800200605.
Liu, Y. et al. Synthesis, Stability, and Cellular Internalization of Gold Nanoparticles Containing Mixed Peptide-poly (ethylene glycol) Monolayers. 2007 Anal. Chem. 79, 2221-9.
Malone, B. Blood Glucose Meters: Is FDA Ready to Tighten Up Accuracy Standards? Clinical Laboratory News 2010; 36(5):1-4.
Maskow, T. et al., "Chip calorimetry for the monitoring of whole cell biotransformation", Journal of Biotechnology, Apr. 2006 (available online Nov. 2005), vol. 122, No. 4, pp. 431-442 DOI:10.1016/j.jbiotec.2005.10.008.
Mandakumar, V. et al., "A methodology for rapid detection of *Salmonella typhimurium* using label-free electrochemical impedance spectroscopy", Biosensors and Bioelectronics, Dec. 2008, vol. 24, No. 4, pp. 1039-1042 DOI:10.1016/j.bios.2008.06.036.

Nassar, A. et al., "Diabetes in the Desert: What Do Patients Know about the Heat?", Journal of Diabetes Science and Technology, Sep. 2010, vol. 4, No. 5, pp. 1156-1163 DOI:10.1177/193229681000400514.
Nassar, A. et al., "Outpatient-to-Inpatient Transition of Insulin Pump Therapy: Successes and Continuing Challenges", Journal of Diabetes Science and Technology, Jul. 2010, vol. 4, No. 4, pp. 863-872 DOI:10.1177/193229681000400415.
Newman, J. et al., "Home blood glucose biosensors: a commercial perspective", Biosensors and Bioelectronics, Jun. 2005, vol. 20, No. 12, pp. 2435-2453 DOI:10.1016/j.bios.2004.11.012.
Pan, Y. et al., "Electrochemical immunosensor detection of urinary lactoferrin in clinical samples for urinary tract infection diagnosis", Biosensors and Bioelectronics, Oct. 2010 [available onlone Jul. 2010], vol. 26, No. 2, pp. 649-654 DOI:10.1016/j.bios.2010.07.002.
Petrou, P. et al., "BioMEMS device with integrated microdialysis probe and biosensor array", Biosensors and Bioelectronics, Oct. 2002, vol. 17, No. 10, pp. 859-865 DOI:10.1016/S0956-5663(02)00055-6.
Protopapa, E. et al., "Interaction of self-assembling β-sheet peptides with phospholipid monolayers: The effect of serine, threonine, glutamine and asparagine amino acid side chains", Electrochimica Acta, Mar. 2010, vol. 55, No. 9, pp. 3368-3375 DOI:10.1016/j.electacta.2010.01.023.
Rosu, M. et al., "Oxidation of glucose in suspensions of moderately hydrophobized palladium catalysts", Chemical Engineering Science, Jan. 2010 (available online May 2009), vol. 65, No. 1, pp. 220-225 DOI:10.1016/j.ces.2009.05.002.
Schalken, J., "Towards Early and More Specific Diagnosis of Prostate Cancer? Beyond PSA: New Biomarkers Ready for Prime Time", European Urology Supplements, Jan. 2009 (available online Nov. 2008), vol. 8, No. 3, pp. 97-102 DOI:10.1016/j.eursup.2008. 10.007.
Schlatter, S., "Bio-sensing textile based patch for sweat monitoring", University of Rhode Island Spring 2009 Seminar Abstracts, 2009, 1 page.
Scholle, A., et al. "Sequence of the mgIB gene from *Escherichia coli* K12: comparison of wild-type and mutant galactose chemoreceptors." Molecular and General Genetics MGG 208.1 (1987): 247-253.
Shakila, V. et al. Preparation of Gold Nanoislands on Various Functionalized Polymer-modified Glass and ITO for Electrochemical Characterization of Monolayer Assembly of Alkanethiols. 2007 J. Solid State Electrochem. 11, 296-302.
Slot, J. W. et al. A New Method of Preparing Gold Probes for Multiple-labeling Cytochemistry. 1985 Eur. J. Cell Biol. 38, 87-93.
Smith, N. et al., "New Ultrasound Insulin Patch Could Eliminate Needles" [online], The Whitaker Foundation, Feb. 2003 [retrieved Apr. 13, 2021 from archive.org, as it appeared on Feb. 12, 2003], retrieved from the internet: URL:https://web.archive.org/web/20030212123023/http://www.whitaker.org/news/insulinpatch.html.
Steuber, T. et al., "Circulating biomarkers for prostate cancer", World Journal of Urology, Apr. 2007, vol. 25, pp. 111-119 DOI:10. 1007/s00345-007-0160-0.
Stockton, L. et al., "Development and Implementation of Evidence-Based Guidelines for IV Insulin: A Statewide Collaborative Approach", Insulin, Apr. 2008, vol. 3, No. 2, pp. 67-77 DOI:10.1016/S1557-0843(08)80018-8.
Sun, C-P. et al., "Rapid, species-specific detection of uropathogen 16S rDNA and rRNA at ambient temperature by dot-blot hybridization and an electrochemical sensor array", Molecular Genetics and Metabolism, Jan. 2005 (available online Dec. 2004), vol. 84, No. 1, pp. 90-99 DOI:10.1016/j.ymgme.2004.11.006.
Swift, J. et al. Efficient Self-assembly of Archaeoglobus Fulgidus Ferritin Around Metallic Cores. 2009 Langmuir 25, 5219-5225.
Tang, H. et al., "A label-free electrochemical immunoassay for carcinoembryonic antigen (CEA) based on gold nanoparticles (AuNPs) and nonconductive polymer film", Biosensors and Bioelectronics, Jan. 2007 (available online Jun. 2006), vol. 22, No. 6, pp. 1061-1067 DOI:10.1016/j.bios.2006.04.027.
Tangkuaram, T. et al., "Sensitive and rapid electrochemical bioassay of glycosidase activity", Analyst, Jul. 2006, vol. 131, No. 8, pp. 889-891 DOI:10.1039/B605943K.

(56) References Cited

OTHER PUBLICATIONS

Tunis, S. et al., "Self-monitoring of blood glucose (SMBG) for type 2 diabetes patients treated with oral anti-diabetes drugs and with a recent history of monitoring: cost-effectiveness in the US", Current Medical Research and Opinion, 2010 (available online Nov. 2009), vol. 26, No. 1, pp. 151-162 DOI:10.1185/03007990903400071.

U.S. Appl. No. 16/612,270, filed Nov. 8, 2019, LaBelle et al., titled Point-Of-Care Apparatus and Methods for Analyte Detections Using Electrochemical Impedance or Capacitance.

Vasan, R., "Biomarkers of cardiovascular disease: molecular basis and practical considerations", Circulation, May 2006, vol. 113, No. 19, pp. 2335-2362 DOI:10.1161/CIRCULATIONAHA.104.482570.

Wang, M. et al., "Application of impedance spectroscopy for monitoring colloid Au-enhanced antibody immobilization and antibody-antigen reactions", Biosensors and Bioelectronics, Jan. 2004 (available online Sep. 2003), vol. 19, No. 6, pp. 575-582 DOI:10.1016/S0956-5663(03)00252-5.

Westphal, S. et al., "Managing Diabetes in the Heat: Potential Issues and Concerns", Endocrine Practice, May 2010, vol. 16, No. 3, pp. 506-511 DOI:10.4158/EP09344.RA.

Williams, M. et al., "Hemodialyzed type I and type II diabetic patients in the US: Characteristics, glycemic control, and survival", Kidney International, Oct. 2006, vol. 70, No. 8, pp. 1503-1509 DOI:10.1038/sj.ki.5001789.

Wu, J. et al., "Electric Field-Driven Strategy for Multiplexed Detection of Protein Biomarkers Using a Disposable Reagentless Electrochemical Immunosensor Array", Analytical Chemistry, Aug. 2008, vol. 80, No. 15, pp. 6072-6077 DOI:10.1021/ac800905k.

Ye, Y. et al., "Direct Electrochemical Monitoring of RNase Activity", Electroanalysis, Apr. 2008, vol. 20, No. 8, pp. 919-922 DOI:10.1002/elan.200804172.

Yu, X. et al., "An impedance array biosensor for detection of multiple antibody-antigen interactions", Analyst, Apr. 2006, vol. 131, No. 6, pp. 745-750 DOI:10.1039/B517148B.

Zhang, B. et al., "A novel multi-array immunoassay device for tumor markers based on insert-plug model of piezoelectric immunosensor", Biosensors and Bioelectronics, Aug. 2007, vol. 23, No. 1, pp. 19-25 DOI:10.1016/j.bios.2007.03.007.

Zhang, P. et al., "Global healthcare expenditure on diabetes for 2010 and 2030", Diabetes Research and Clinical Practice, Mar. 2010, vol. 87, No. 3, pp. 293-301 DOI:10.1016/j.diabres.2010.01.026.

Ziemer, D. et al., "Diabetes Management in Urban African Americans: Review of a Public Hospital Experience", Ethnicity and Disease, 2008, vol. 18, No. 3, pp. 336-341.

\* cited by examiner

Input, output ∝ blood glucose concentration

Input, output ∝ Insulin concentration

Input, output ∝ blood glucose AND Insulin concentrations

METHODS AND DEVICE FOR TUNING MULTIPLEXED MARKERS FOR DISEASE ASSAY

RELATED APPLICATIONS

This application is a 371 application of PCT/US2011/043652 filed Jul. 12, 2012 which claims priority based on U.S. Provisional Application No. 61/363,394, which was filed Jul. 12, 2010. The entire text of the aforementioned applications are incorporated herein by reference.

FIELD OF THE INVENTION

The present invention relates to a diagnostic device and methods of using the same for diagnostic assays for monitoring the presence of biological samples wherein the device allows for the determination of at least two assay components on one sensor.

BACKGROUND OF THE INVENTION

The use of biological markers as diagnostic aids is well-established. Likewise various serum tumor-associated proteins are recognized as useful biomarkers in detecting cancer at early stages, monitoring disease progression, and determining therapeutic response. For example, prostate specific antigen (PSA) is used in the diagnosis of prostate cancer. However, a single biomarker is often insufficient to specifically and sensitively identify a given disease. Indeed, PSA presents this problem well; it is a 33 kDa protease that is present in serum at a normal concentration of 0-4 ng/ml but is elevated to between 5 ng/ml and 10 ng/ml in subjects that have prostate cancer. However, elevated levels of PSA can also be caused by prostate infection, irritation, and many other physiological conditions.

The specificity of a given biomarker can be defined as:

$$\text{Specificity} = \frac{\text{True-negatives}}{\text{False-positives} + \text{True-negatives}}$$

where 100% specificity means that all subjects without the disease are diagnosed as not having the disease. Thus specificity is related to a biosensors ability to be used as a diagnostic tool whereas sensitivity is defined as:

$$\boxed{\text{Sensitivity}} = \frac{\text{True-positives}}{\text{True-positives} + \boxed{\text{False-negatives}}}$$

where 100% sensitivity means that all subjects that have the disease are diagnosed as having the disease. As such, sensitivity is a limiting factor allowing for a biosensor to be used as a screening aid. With the use of PSA as an exemplary biomarker, it is seen that this biomarker lacks both sensitivity and specificity to accurately detect subjects at risk of prostate cancer. Indeed, it is recognized that the PSA test alone is approximately 21% sensitive and 94% specific. To combat the problem of lack of sensitivity, the PSA test is usually combined with a second test for the disorder in which other biomarkers are used in conjunction with PSA to more accurately diagnose prostate cancer. Such orthogonal assays in which multiple markers (or tests) are assayed is now commonplace not only in the diagnosis of prostate cancer but in many other diseases.

In addition to cancer, another disorder that requires vigilant monitoring is diabetes. Most diabetic patients are encouraged to self monitor blood glucose (SMBG) three to six times daily. The actual function of the device is an electrochemical detection of the oxidation of glucose into gluconic acid called using a glucose oxidase enzymatic assay called amperometry. In the amperometric mode, a voltage is applied on a two or three electrode while recording the current produced from the enzymatic reaction, typically with the aid of a mediator reagent. After a fixed amount of time, a current reading is taken, which in turn is correlated to a level of blood glucose. Other SMBG device may change the enzyme, potential, or numbers of electrodes, but all employ the same amperometric sensing strategy. A gold standard method to observe a patient's average blood sugar is to look at the accumulated glycosylated hemoglobin (HbA1c) in a patient's blood which yields a two to three month average and are recommended to take this test only four times a year, however few do. This is a similar problem to SMBG in general, due to pain associated with finger pricking this number is actually lower than desired. In diabetes, some research is leading towards using multiple markers to more accurately monitor type II diabetes. By using metabolic, inflammatory, immunological markers, among others, it is felt a more controlled method of diabetes management might be found. Markers such as C-reactive protein (CRP), HbA1c, glucose, insulin, and interleukin-2 receptor A (IL-2RA) integrated onto a single sensor are being considered (FIG. 1).

Nevertheless, the use of multiple biomarkers to accurately diagnose a given disorder typically requires more than one assay type, complex instrumentation and various different assay reactions to arrive at a single diagnosis. Thus there is a need for an efficient multiplex assay system in which multiple biomarkers can be monitored in a single analysis step. There are many technologies that can be used to study multiple markers, typically called arrays or microarrays. The technology to detect multiple markers using microarrays ranges from mechanical, optical, thermal, and electrochemical. However, each one of these techniques either requires multiple sensors, wells, platforms, and/or the use of labeling the target of interest.

Biosensors that use impedance measurements to detect the presence of pathogens have been described (see e.g., U.S. Pat. No. 6,846,639 and WO 2007104058). In U.S. Pat. No. 6,846,639, there is a description of a method of detecting pathogens attached to specific antibodies by measuring change in impedance between pairs of spaced electrodes on which antibody coated beads amplifying the change in impedance as a manner to detect whether the antibodies are bound to pathogens or not. This demonstrates that impedance measurements can be taken on electrodes and used as a method of detecting whether the antibodies are bound to a specific antigen.

In the case of the technology behind most SMBG devices, using amperometric mode, the only means to monitor multiple markers on a single device typically requires the use of labels, which often can lead to user error. In potentiometric mode, where current is driven onto the electrode and the potential developed is quantified, labels are also required to perform multiplexing.

The last of the three electrochemical techniques, electrochemical impedance spectroscopy (EIS), where an alternating signal rides on top of bias potential while frequencies from sub or single Hz to MHz are scanned. In EIS, the ratio of the input signal to the output signal develops the impedance (Z, in ohms), and with the change (if any) in phase (Φ) between input and output, real (Z') and imaginary (Z") impedances can be calculated from the equations below:

$$Z' = Z \cos(\Phi) \quad (1)$$

$$Z'' = Z \sin(\Phi) \quad (2)$$

From this data, typically a Nyquist graph is plotted, this is the real (Z') impedance plotted as the x-axis, against the negative of the imaginary (–Z") impedance and looks, typically, like a semicircle (FIG. 2) in the case of a Randles model. These plots tend to be "information rich" as the figure shows. The starting point of the curve, near the origin, reflects the impedance at the highest frequencies and on the x-axis, the intersection is the solution resistance of the system, or $R_s$. As the graph moves towards the right, or lower frequencies, where the graph touches the x-axis again. At this point, the low frequencies, the impedance is dependent upon electron transfer resistance, $R_{et}$. Approximately halfway between these two points is the maximum, at this frequency, the frequency is related to the inverse of 2 times pi times the electron transfer resistance time the double layer capacitance, $C_{dl}$. These parameters can be in turn, modeled using equivalent circuit diagrams to determine system behavior at any frequency. Note, there are many types of Nyquist, ranging from constant phase element (CPE), to Warburg, among other, depending upon surface imperfections or diffusion limited systems to name a few.

EIS can be performed in a label-free manner, for small molecules, proteins, or whole cell with the target molecules or cells exhibiting a unique frequency upon binding. In the case of breast cancer, the Thompson-Frederick (TF) antigen has long been thought to be a good indication of breast cancer in nipple aspirate fluid. Since nipple aspirate fluid is considered a minimally invasive medium, it was selected for biosensor development for breast cancer screening using label-free EIS. This resulting sensor demonstrated that the sugars on the TF antigen and the molecular recognition elements (sugar binding proteins or lectins to provide for highly specific binding elements) exhibited a maximal detection response at 176 Hz. Development of a label-free diagnostic aid for multiple sclerosis using interleukin-12 (IL-12) as a biomarker demonstrated a 5 Hz signal between IL-12 and the corresponding antibody. Whole cell biosensors for the determination of bacterial infection, such as *Salmonella typhimurium* have also been developed. Unique frequencies have been determined to be at 10 Hz for the interaction of *S. typhimurium* with its corresponding antibody.

Enhancements to EIS have been made over the years, typically in signal amplification, such as the use of colloidal gold, or gold nanoparticles (AuNPs). Some researchers have demonstrated an amplification affect by using AuNPs in EIS[15] where the addition of the AuNP (and a secondary label step) allows for a more sensitive signal to be produced due to an altered electrical effect (e.g. electron transfer resistance) on the system. Recently this multiplexed sensor array design was implemented for various inflammatory markers and the exact nature of the overlapping problem was verified (Fairchild, 2009). Five markers, IL-2, IL-10, IL-12, tumor necrosis factor-alpha (TNF-α), and interferon-gamma (IFN-γ) were studied. The results of the study showed that some of these markers were very close to overlapping, with 5, 9.77, 17.44, 31.5, and 117.2 Hz for the IL-12, IFN-γ, TNF-α, IL-2, and IL-10 markers, respectively. It would be almost impossible to differentiate, label-free, these five markers on a single device due to the closeness of the maximal frequencies. For example, if IL-12 and IFN-γ were to be detected on the same device, without any "adjustment" present state-of-the-art methods could not differentiate a change in signal due to one and/or the other.

To date, the only mechanism for monitoring multiple biomarkers sensing has been to use more than one sensor, and this has been demonstrated with EIS as well. However, again, the compliance issue with single sensor finger pricking would not tolerate multiple sensors requiring multiple finger pricks per day. Thus, there remains a need for an efficient electrochemical technique that allows the monitoring of multiple biomarkers in a single multiplexed assay.

BRIEF SUMMARY OF THE INVENTION

In specific aspects, the invention relates to a multi-marker electrochemical impedance spectroscopy sensor comprising a plurality of molecular recognition elements wherein the sensor comprises multiple different molecular recognition element types, wherein each molecular recognition element type is conjugated with a tuning element that is specific for the molecular recognition element type, wherein the presence of the tuning element on the molecular recognition element type alters the frequency of the molecular recognition element type such that it is at a detectably different frequency to the frequency of other molecular recognition element types on the sensor.

The molecular recognition element type may independently be any agent that acts as a binding partner for another agent to be screened. Thus, such a molecular recognition element may be independently selected from the group consisting of antibodies, enzymes, receptors, and ligands or antigens, DNA, RNA, peptides, and synthetic antibodies.

In some sensors, all of the molecular recognition element types are comprised of one type of binding partner. For example, all of the molecular recognition element types are either all antibodies, all enzymes, all receptors; or all ligands, all antigens, all DNA molecules, all peptides all antibody fragments or all antibodies.

In other sensors, the sensor may be comprised of disparate types of molecular recognition element types all deposited on the electrode for example, the molecular recognition element types on the sensor are a mixture of antibodies, enzymes, receptors and ligands and the like. Ideally, each of these disparate types are related in that they all detect the same or similar disease state. Thus, a sensor of the present invention may be one in which there are antibodies, enzymes, receptors and ligands and the like all of which are capable of detecting one or other agent that is indicative of a specific type of cancer, diabetes, cardiovascular disease, autoimmune disease or the like.

In specific embodiments, the tuning element is selected from the group consisting of magnetic nanobeads, polystyrene beads, carbon nanotubes, nanowires, nanocolloids, nanoparticles, nanorods, quantum dots, nanocrystals, liposomes, silica beads, latex beads, gold colloids or other structures with dimensions less than one micron. More preferably, the tuning element is selected from nanoparticles, colloids, nanorods or nanobeads comprised of a material selected from the group consisting of gold, silver, titanium, palladium, platinum, nickel, copper, manganese, titanium, and oxides thereof.

In some embodiments, the tuning element is directly affixed to the molecular recognition element. In other embodiments, the tuning element is affixed to the molecular recognition element through a peptide linker or physical adsorption. In specific preferred embodiments, the tuning label is a colloids, nanorods or nanobeads of 2-20 nm in diameter. Preferably, such a nanoparticle is comprised of a material selected from the group consisting of gold, silver, titanium, palladium, platinum, nickel, copper, manganese, titanium, and oxides thereof The tuning element may be affixed to the molecular recognition element through conventional conjugation chemical techniques known to those of skill in the art. For examples, the molecular recognition element may be conjugated to the tuning element through a functional group on the label wherein the functional group is selected from the group consisting of biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin and biotin binding proteins.

In specific embodiments, the molecular recognition element is affixed to the sensor surface through a linkage with the tuning element wherein the tuning label is affixed to the sensor surface through a functional group.

The functional group used for affixing the tuning element to the sensor surface may be any conventional functional group such as for example, biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin and biotin binding proteins and combinations of the aforementioned.

The invention also relates to a biosensor device capable of detecting the presence of at least two different biomarkers comprising an electrically conductive single electrode operatively coupled to an impendence analyzer for monitoring the change in resistive impedance of the electrode in response to an applied current, the single electrode comprising a plurality of molecular recognition elements wherein the device comprises at least two types of different molecular recognition elements, wherein each molecular recognition element type is conjugated with a tuning element that is specific for the molecular recognition element type, wherein the presence of the tuning element on the molecular recognition element type alters the frequency of the molecular recognition element type such that it is at a detectably different frequency to the frequency of other molecular recognition element types on the electrode.

Also contemplated herein is a method of determining the presence of a plurality of biomarkers in a biological sample, comprising: contacting the sample with a sensor of the invention or a device comprising such a sensor; determining the impedance measurement from the electrode to provide the multiplexed frequency; de-multiplexing the multiplexed frequencies to identify the frequency attributable to each individual biomarker from the plurality of biomarkers detected.

In such methods, measuring impedance may be performed by any conventional impedance measuring apparatus or device. Typically, the impedance from the sensor is taken by application of from 0.1 Hz to 105 Hz frequency. The AC and DC offsets may be varied in accordance with standard impedance measurement techniques. For example, the frequency may be applied with an amplitude of 5 mV sweeps using a 250 mV DC offset and 5 mV AC potential. Notably, these DC offsets and AC potential are simply examples.

The methods of the invention may be used in the detection and diagnosis of virtually any disease state for which a marker is known. Exemplary such diseases include but are not limited to inflammatory disease, autoimmune disease, metabolic disease, disorder of signaling, metabolic storage disease and the like. So for example, the methods of the invention may be used to detect the presence of multiple biomarkers for diseases such as cancer, bacterial infection, viral infection, cardiovascular disease, diabetes, irritable bowel syndrome, Sjorgen's disease discoid lupus erythematosus, conjunctivitis, systemic lupus erythematosus (SLE), autoimmune hepatitis, cleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, and pulmonary fibrosis, multiple sclerosis (MS), and Crohn's disease, all of which have been extensively characterized as having specific markers associated therewith. The skilled person will be aware that numerous other diseases and their associated markers may be amenable to the multiplex detection methods described herein.

In a specific example, the disease may be prostate cancer which includes among other markers such as PSA, PCA3, GOLPH2, and SPINK1. The methods and devices of the present invention are specifically performed to detect or diagnose prostate cancer, provide a prognosis for the disease or otherwise monitor treatment of the disease by preparing devices of the invention that comprise sensors that comprise molecular recognition elements for at least two such markers and monitoring the presence of such markers in biological samples of the subject either initially to diagnose the disorder, and/or during and after therapy to provide a prognosis of the efficacy of the specific therapy.

Similarly, another specific disease that may be detected is diabetes, which includes among other characterized markers, the biomarkers CRP; glucose; insulin; TRIG; GPT; HSPA1B; IGFBP2; LEP; ADIPOQ; CCL2; ENG; HP; IL2RA; SCp; SHBG; and TIMP2. The methods and devices of the present invention are performed by preparing devices of the invention that comprise sensors that comprise molecular recognition elements for at least two such markers. The methods and devices of the present invention are specifically performed to detect or diagnose a diabetic condition, provide a prognosis for the disease or otherwise monitor treatment of the disease by preparing devices of the invention that comprise sensors that comprise molecular recognition elements for at least two such markers and monitoring the presence of such markers in biological samples of the subject either initially to diagnose the disorder, and/or during and after therapy to provide a prognosis of the efficacy of the specific therapy.

In some embodiments, the disorder or condition to be detected is stress and the biomarkers for stress are selected from the group consisting of pH, pO2, pCO2; epinephrine, norepinephrine, dopamine; cortisol, lactate and glucose, heart rate, EKG, respiration, blood pressure, and hydration.

BRIEF DESCRIPTION OF SEVERAL VIEWS OF THE DRAWINGS

FIGS. 10B, 10C and 10D Using the same reaction as in FIG. 10A but changing input voltage to a more complex signal (10B), multiple indicators such as glucose and insulin (10C) can be measured simultaneously (10D).

DETAILED DESCRIPTION OF THE INVENTION

Figure 1:
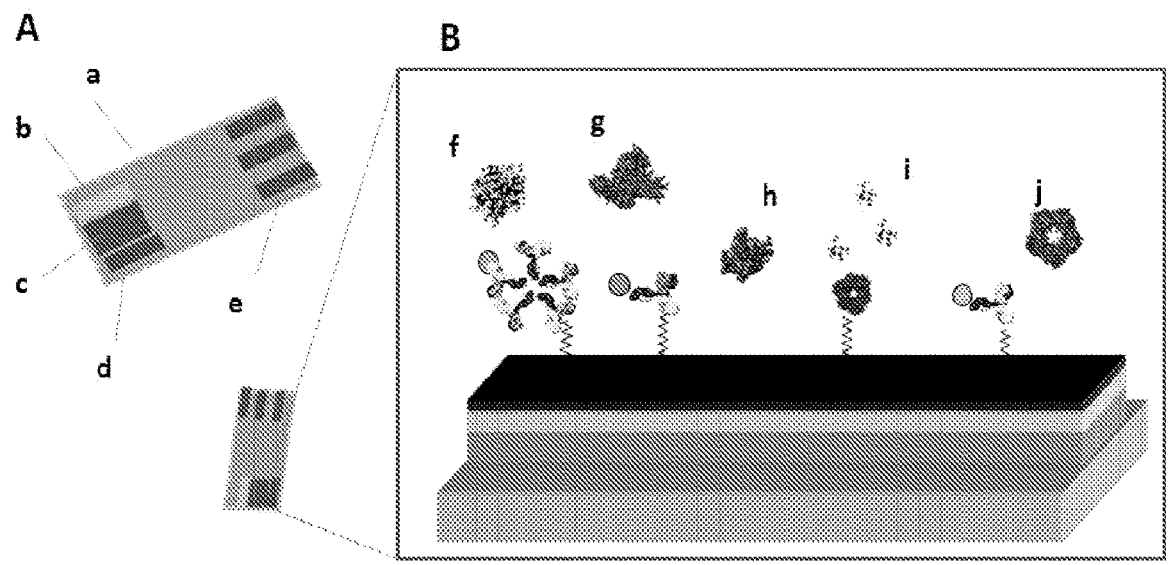
FIG. 1 Conceptual diagram of sensor (A) showing sensor substrate (a) on which Ag/AgCl reference (b), gold working (c), gold counter (d) electrodes and electrical leads (e) are fabricated on. Cross section of sensor surface (B) with 5 possible target systems under study simultaneously. These targets could range from: HbA1c (f) detected by tuned monoclonal antibody, IL-2RA (g), insulin (h) using its inherent electroactive nature for detection, enzymatic detection of glucose (i) using GDH-FAD, and finally hsCRP detection (j) using tuned monoclonal antibody assay all simultaneously on a single strip sensor.
Figure 2:
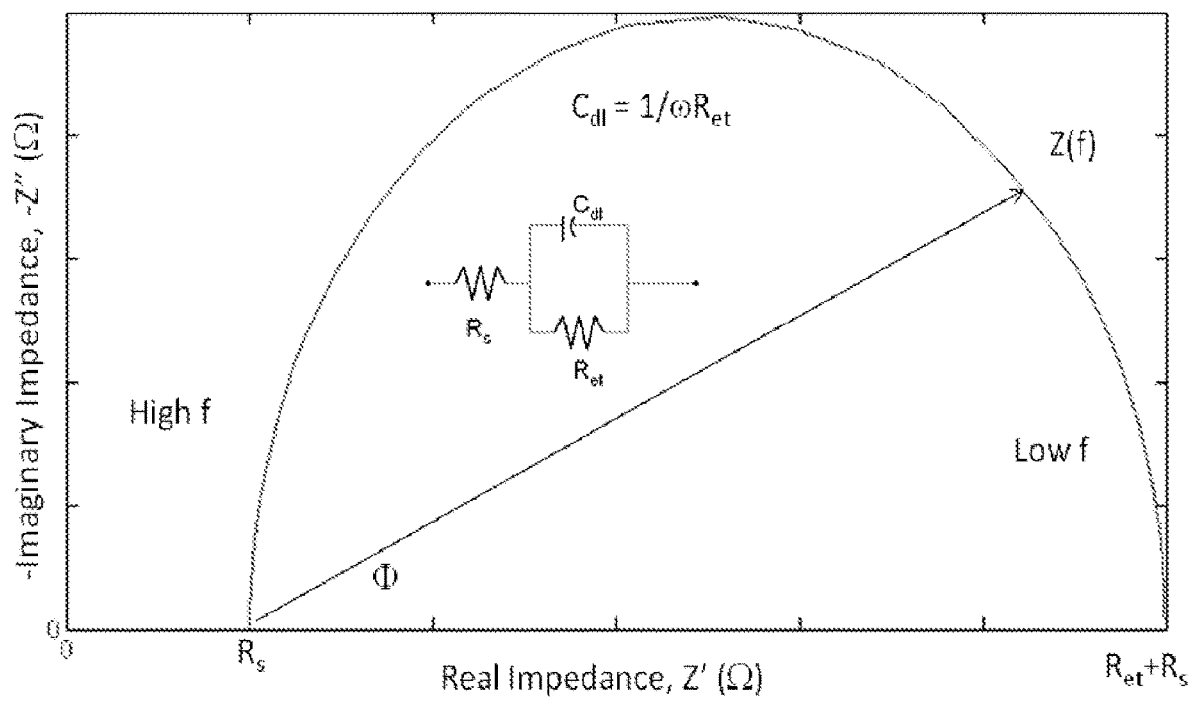
FIG. 2: Nyquist curve plot of imaginary versus real impedance demonstrating key parameters of interest. Inset: simplified Randles cell equivalent circuit diagram for Nyquist curve presented.

In the present invention, there is provided for the first time a sensor that is capable of detecting a plurality of biomarkers in a single assay. More particularly, the sensor surface comprises as many molecular recognition element types as biomarkers that are to be detected wherein the molecular recognition element types are bound to a tuning label. Each of these molecular recognition elements when they are bound to their specific biomarker targets have a particular frequency that can be detected using electrochemical impedance spectroscopy. However, under standard conditions, the electrochemical impedance of two different target-molecular recognition elements is too close together to allow for sufficient separation of impedance signal between two different target-molecular recognition elements. The present invention shows that it is possible to alter the signals of the different target-molecular recognition elements such that the signal from one target-molecular recognition element is tuned away from the other target-molecular recognition element. The inventors showed that if the molecular recognition element is conjugated with a tuning particle that will have sufficient impact to reliably alter that electrochemical impedance of a target-molecular recognition element, then multiple different target-molecular recognition elements can be detected on a single sensor.

All that is required is that each "type" of molecular recognition element be conjugated with the same label such that when that "type" of molecular recognition element is bound to its target all of the target-molecular recognition elements of that type will have the same frequency. The term "type" when used in referring to "type of molecular recognition element" is used to refer to a target specific molecular element. Hence, a molecular recognition element that recognizes IL-2 as a target will be different from a molecular recognition element that recognizes IL-6.

The "tuning element" is any entity that can be bound to the molecular recognition element to sufficiently alter the frequency of electrochemical impedance of the type of molecular recognition element to which it is bound as compared to another type of molecular recognition element that is on the same sensor. "Tuning" works by inputting a signal (or frequency) specific to a capture element (i.e. an antibody or enzyme) so that binding of that capture element to a biological marker can be maximized. In the present invention the inputted signals for several capture elements are combined into a single signal that allows for detection of multiple biological markers simultaneously (and with high sensitivity/specificity). The image and explanation shown in FIG. 10 compares the present invention to that of a standard SMBG device.

Since the electrochemical impedance of a target-molecular recognition element is based upon both capacitance and resistance, the tuning elements used in the multi-marker EIS sensor of the present invention could be made of any material that can bind to the enzyme, antibody, receptor (i.e., molecular recognition element). For example, the tuning element may be an entity selected from the group consisting of magnetic nanobeads, polystyrene beads, carbon nanotubes, nanowires, nanocolloids, nanoparticles, nanorods, nanocrystals, liposomes, silica beads, latex beads, gold colloids or other structures with dimensions less than one micron. In specific preferred embodiments, the tuning element preferably is selected from nanoparticles, colloids, nanorods or nanobeads comprised of a material selected from the group consisting of gold, silver, titanium, palladium, platinum, nickel, copper, manganese, titanium, and oxides thereof.

Thus, in a multi-marker EIS sensor of the present invention, a first molecular recognition element will be attached to a first tuning element and a second molecular recognition element will be attached to a second tuning element wherein the first tuning label is sufficiently different from the second tuning element such that the frequency of the electrochemical impedance of the first molecular recognition element is detectably separable from the frequency of the electrochemical impedance of the second molecular recognition element.

While it is preferred that the first and second tuning element are different in kind (e.g., one is a gold nanorod and the second is latex bead), it is contemplated that the size of the tuning element also may be a differentiating factor that allows the molecular recognition element to which the tuning element is attached to have a different frequency than the other types of molecular recognition elements on the same sensor.

In addition, first molecular recognition element type conjugated with a tuning element may be caused to have a frequency of electrochemical impedance that is different from another molecular recognition element type on the same sensor by varying the length of attachment between the molecular recognition element type and the sensor surface.

In specific embodiments, the tuning element is conjugated to the molecular recognition element type through a direct linkage or physical adsorption. In other embodiments, the tuning element is attached to the molecular recognition element type through a peptide linker. In still other embodiments, the tuning element is attached to the molecular recognition element type through a functional group such as biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin and biotin binding proteins. Varying the length of these functional groups may vary the frequency of electrochemical impedance.

There are various formats of attaching the molecular recognition element to the surface of the sensor. In one embodiment, the molecular recognition element is attached directly to the surface of the sensor and already conjugated with the tuning element in any part of the molecular recognition element that does not interfere with the binding thereof to its target.

In another embodiment, the molecular recognition element is attached to the tuning element and the tuning element is attached to the surface of the sensor. In such embodiments, the tuning element may be directly attached to the molecular recognition element and attached to the surface of the sensor through a functional group such as a biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin biotin binding proteins, hydrogels, PAA (poly acrylic acid), PVA (poly vinyl alcohol), Chitosan, PNIPAM (Poly-N-isopropyl acrylamide), substituted PNIPAM (including PNIPAM-aa (poly-N-isopropyl acrylamide-acrylic acid), PNIPAM-allylamine (Poly-N-isopropyl acrylamide-allylamine), and PNIPAM-SH), PAMAM (Polyamidoamine), PEG (Poly ethylene glycol), alginic acid, HPC (hydroxyl propyl cellulose), or a combination thereof. Alternative, the tuning element may be attached to the molecular recognition element through a linker that extends the distance and hence further alters the frequency of electrochemical impedance.

The molecular recognition element may be any entity that recognizes a binding partner. For example, the molecular recognition may be a monoclonal antibody that recognizes a specific antigen, it may be an enzyme specific for a particular substrate or it may a receptor that is specific for a particular ligand. Indeed, the molecular recognition element may be any agent that binds to a specific partner, examples of other such partners include but are not limited to peptides, antibody fragments, synthetic antibodies, DNA, ssDNA, RNA, etc. It should be understood that in order to improve sensitivity of a given sensor there will be a plurality of individual molecular recognition elements of each type on the sensor. For example, where the first molecular recognition element is a monoclonal antibody against IL-2 and the second molecular recognition element is a monoclonal antibody against IL-6, there will be multiple individual anti-IL-2 antibodies on the sensor and multiple individual IL-6 antibodies on the sensor.

In certain preferred embodiments, the molecular recognition elements are all antibodies for different antigens. However, it should be understood that the versatility of the multi-marker EIS sensor of the invention is such that the sensor may have a first molecular recognition type that is an antibody and another molecular recognition type that is an enzyme or a receptor. It should also be noted that this sensor may be prepared with any antibody/antigen couple. Also it should be noted that where it is desirable to detect the presence of an antibody in a sample, the biosensor may be made with the antigen affixed to the sensor.

Simply by way of example, the skilled person would understand that a multi-marker EIS sensor for monitoring diabetes could be prepared that has molecular recognition elements for markers such as glucose, insulin, CRP, IL-2RA, and HbA1c. In such a sensor glucose could be detected by the molecular recognition element of GDH-FAD assay or a glucose/galactose binding protein ("GGBP") as previously described (Scholle, et al., Mol. Gen. Genet 208:247-253 (1987)), whereas IL-2RA could be detected by a molecular recognition element that is a monoclonal antibody specific for IL-2RA.

For the purposes of the present invention any target that can be detected using the molecular recognition elements can be any antigen or analyte that is indicative of a particular disease. Biomarkers that may be particularly useful to test include but are not limited to; angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-I; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; C-reactive protein, pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example CRP; glucose; insulin; TRIG; GPT; HSPA1B; IGFBP2; LEP; ADIPOQ; CCL2; ENG; HP; IL2RA; SCp; SHBG; and TIMP2.

The devices of the present invention will be particularly useful in monitoring diabetes mellitus. In such devices, the markers for diabetes preferably are glucose, insulin, Interleukin 2 receptor alpha (IL2-RA), C-reactive protein (CRP) and glycated hemoglobin (HbA1c).

Additional devices may be prepared and useful for monitoring of stress signals. There are many types of markers of note that one could use to measure stress including but not limited to pH, pO2, and pCO2; Catecholamines—epinephrine, norepinephrine, and dopamine; Cortisol and Lactate and glucose as well as parameters such as Heart rate, EKG, respiration, blood pressure, and hydration.

The device may be used for obtaining trace fluid samples from a biological surface for electrochemical analysis and used thereof for detecting analytes in such trace fluids. The device can be used to collect tears from the surface of the eye or fluid from the surface of open wounds (e.g. ulcers). Those samples can be processed to detect metabolic products such as glucose, lactate, uric acid, ascorbic acid, catecholamines such as norepinephrine, epinephrine, and dopamine, pH, $O_2$, ions such as sodium and calcium, whole human cells, pathogens including bacteria, fungi, parasites, and viral particles, metal ions such as zinc, and protein biomarkers such as inflammatory cytokines.

Proteins and other biomarkers for detection and diagnosis of disease and other health states including but not limited to inflammatory cytokine proteins and antibody expression can also be monitored by the present invention. Biological fluids may be from any source including epithelial surface sampling sites for medical assessment including but not limited to infections, ulcers, lacerations, burns, and oral cavities, sweat, urine, blood, and saliva. In some embodiments, the biological fluid tested could be a surgically accessible fluid from the surfaces of internal tissue and organs for analysis and medical treatment including but not limited to hormone excretions from glands, neurotransmitters from nerves and tissues, and various cancerous tissue.

The device also may be used to monitor of analytes from alternate biological sources including but not limited to cell cultures, animal samples, and bioreactors or to monitor environmental analytes including but not limited to pollution particulate sampling and fluid sampling.

In addition, the present invention could be used in a variety of other fields. For example, in environmental and security testing, many compounds of interest are not water-soluble. The fluidics system could potentially be filled with alternate solvents that would allow the device to swab for explosives or chemical contaminants. In security applications the device of the invention may be used for the detection of dangerous agents including but not limited to explosives, chemical agents, and biological agents from various dry surfaces such as luggage and packages and biological surfaces such as skin. In forensic science applications, the device could be used to sample forensic biological materials including but not limited to blood, skin, hair, and other fluids.

The sensor described herein may be housed in any electrochemical sensing device. Preferably, the device is one which has a collection chamber for collecting the sample, such a collection chamber may be one that contains an absorbent hydrogel material that can absorb the material or alternatively the chamber may simply be a cavity into which the biological sample may be directly deposited. Where the sample is in small quantity, the device may further include a fluidic channel connected to the collection chamber at one end and to a sensor device at the other end. The device may be comprised of a compressible housing that allows transfer of fluid collected by the collection chamber to be transferred to be extracted and withdrawn to the sensing chamber upon compression of the device. The specific sensing device of the invention comprises a sensing chamber that contains a sensor comprising a plurality of molecular recognition elements wherein the sensor comprises multiple different molecular recognition element types, wherein each molecular recognition element type is labeled with a tuning element that is specific for said molecular recognition element type, wherein the presence of the tuning element on said molecular recognition element type alters the frequency of said molecular recognition element type such that it is at a detectably different frequency to the frequency of other molecular recognition element types on said sensor. This sensing chamber is operably linked to a processor containing a potentiostat that allows detection of the analyte using electrochemical sensing. More particularly, the processor containing the potentiostat is an electrode system wherein the processing of the fluid comprises applying a voltage to the electrode system to induce an electrochemical reaction between the material that specifically detects the analyte and the analyte in the fluid sample and detecting a current produced by the electrochemical reaction from the contact of the analyte with the material that specifically detects the analyte.

Figure 8:
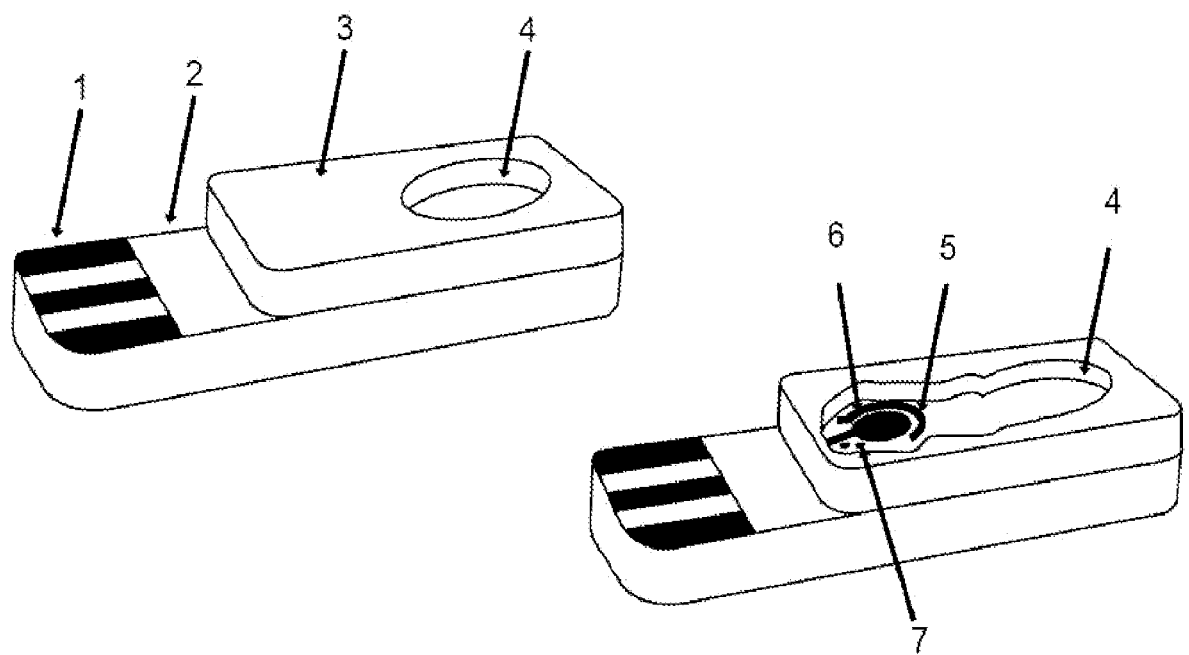
FIG. 8: Schematic of Blood Sensor showing 3 electrode leads (1) for sensor (2) on top of which resides a polymer (3) that creates a sample capture-collection reservoir of patient sample. A cutaway to the right shows how the well (4) passes by capillary action to a sensing region under the polymer (3) that brings the patient sample to the working (5), counter (6), and reference (7) electrodes
Figure 9:
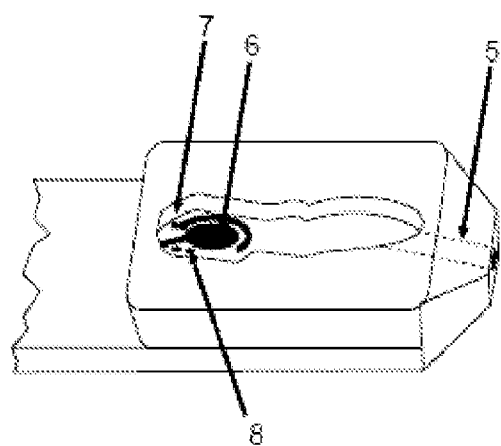
FIG. 9: Schematic of Tear Sensor showing capture inlet (1) contained in a polymer housing (2) which sits upon the sensor (3) with 3 electrode leads (4) for sensor. A cutaway to the left shows how the fluid is passed through a channel (5) to the sensing region containing the working (6), counter (7), and reference (8) electrodes.
Figure 9:
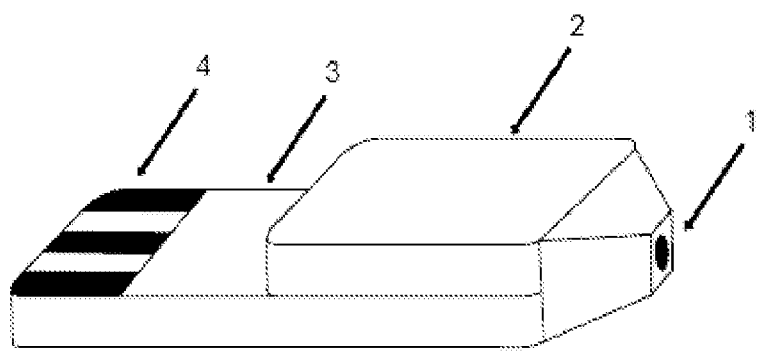
Figure 10A:
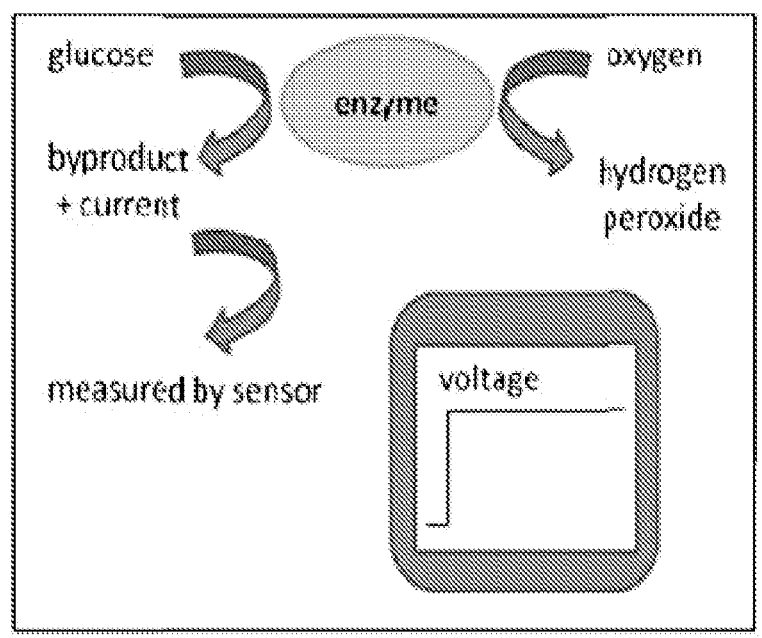
FIG. 10A-10D: A Standard reaction of flucose with enzyme whereby under application of applied voltage, the current produced is measured by the sensor and is proportional to blood glucose concentrations.
Figure 10B:
Figure 10C:
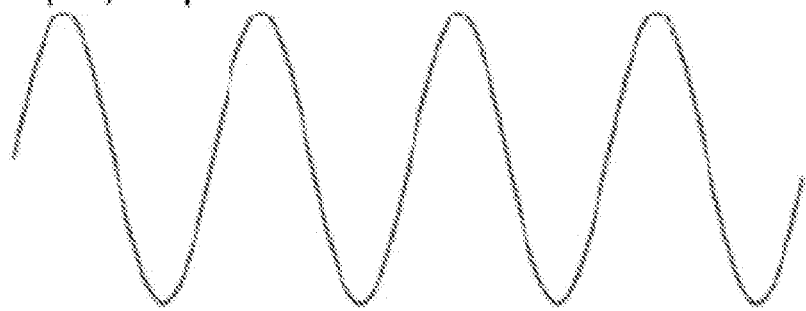
Figure 10D:
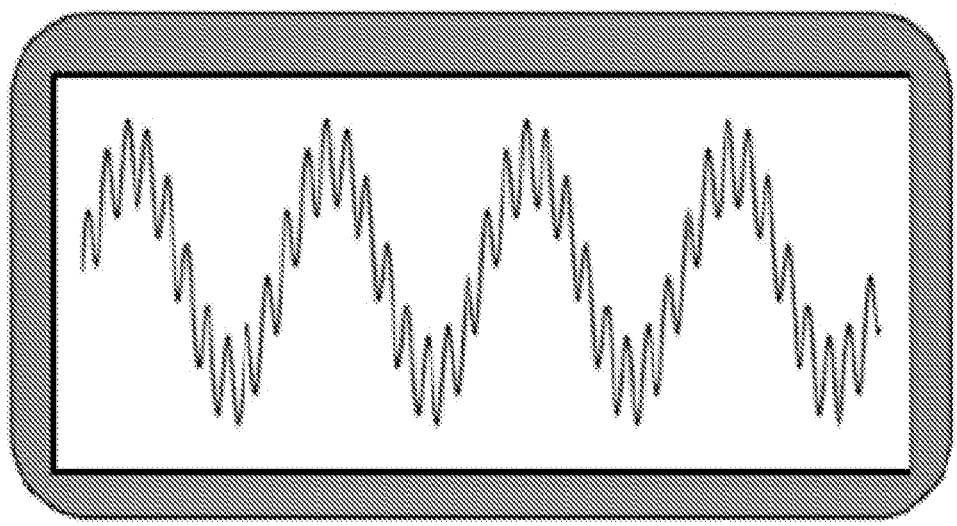

An exemplary device of the invention is depicted in FIG. 8-9. It should be noted however, that the above description of a sensor device is merely one embodiment and the sensors of the present invention may be placed in any conventional biosensing device formats.

Examples: Development of a Single Sensor Multiplexed Marker Assay for Diabetes Management The present example demonstrates the development of multi-marker EIS sensor for the management of diabetes as an exemplary embodiment. Tight glucose control is paramount to a better outcome in diabetes management as well as a means to lower health care associated cost on an overburdened US Health Care System. Noncompliance to self monitoring blood glucose sensor, follow up quarterly HbA1c testing, as well as variability in sensors has led to a lack of tight glucose control. A sensor with the potential to measure multiple markers at once might offer a solution for better glucose control, especially using markers from various systems in the body, inflammatory, immunological, metabolic, for example.

In this example, gold nanoparticles were attached to antibodies for typical inflammatory biomarkers, interleukin-12, on an electrochemical impedance spectroscopy based biosensor. Cross-reactivity and specificity of tuned antibodies was verified using enzyme linked immunosorbent assays. Impedance frequency was quantified by concentration gradients of marker against the device.

The data shown below demonstrate that impedance frequency can be tuned to a frequency four Hertz away from one another for better signal processing. This was obtained with little degradation of the sensitivity of the recognition, no cross reactivity and a high degree of specificity.

Materials/Methods

Gold Nanoparticle-Antibody Conjugation The AuNPs used in this study were prepared according to a method described earlier in the literature (Slot, J. W.; Geuze, H. J. A New Method of Preparing Gold Probes for Multiple-labeling Cytochemistry. 1985 Eur. J. Cell Biol. 38, 87-93). By this method, nanoparticles of 2-20 nm in diameter were prepared. For 5 nm particles, 1 mL of 1% (w/v) $HAuCl_4$ is mixed with 79 mL of deionized (DI) water and heated to 60° C. Meanwhile, a reducing mixture of 4 mL of 1% (w/v) trisodium citrate, 5 mL of 1% tannic acid and 5 mL of 2.5 mM $K_2CO_3$ and 5 mL DI water is brought to 60° C. and added to the gold solution with stirring. Upon observation of the red color, the resulting solution is boiled for 10 more minutes. For larger particles, lower amounts of tannic acid and potassium carbonate were used in equal amounts (down to 0.01 mL for 20 nm particles) while keeping the total reducing solution volume at 20 mL. The final solution containing the particles was cooled down to room temperature and the intensity of plasmon absorption at 520 nm was adjusted to 1 a.u. by centrifugation before use.

Antibodies and antigens in lypholized form were purchased from R&D Systems, Minnesota, MN and were reconstituted in phosphate buffered saline (PBS) which was purchased in tablet form from CalBioChem, La Jolla, Calif., and was dissolved in DI water to yield a working solution of 140 mM NaCl, 10 mM phosphate buffer and 3 mM KCl, pH 7.4 at 25° C.

The conjugation of the antibodies with gold nanoparticles was done according to the following procedures. The minimum amount of antibody required to stabilize the gold nanoparticles in a given solution was determined by mixing a series of concentrations of the protein (10-100 ug/mL, 1 mL) with a milliliter of gold solution and incubation for 5 min. After 5 min, 0.5 mL of 10% (w/v) NaCl was added and the color of the solution is observed. The concentration, just above that of the solution in which the gold changes color to blue from red, was deemed as the minimum required amount for stabilization. Up to 25% excess protein was used above the minimum concentration level to ensure a higher degree of stabilization. The incubation of AuNPs with the correct amount of antibody was done for a total of 20 min at room temperature after bringing the pH of the colloidal suspension to pH 8-9 with $K_2CO_3$, close to the isoelectronic point of the immunoglobulin G (IgG) molecules. The resulting solution was then transferred into an appropriately-sized Beckman Quick-Seal tube and centrifuged in a Beckman-Coulter Optima L-100 XP Ultracentrifuge at 70,000 g at 4° C. for 1 hr to separate unconjugated antibody from the gold-antibody complexes. Dark red colored pellet obtained from centrifugation was then reconstituted in 10 mM phosphate buffered saline. The conjugates were consumed immediately.

Structural assembly of the conjugates was determined by UV-VIS spectroscopy. UV-VIS spectra was gathered on the components prior to and post-conjugation from 450-700 nm from a 1 mL sample using a Shimadzu BioSpec-mini spectrometer after a background of pure buffer was subtracted.

Functional Verification of Gold Nanoparticle-Antibody Conjugates. To verify functional assembly still displayed similar sensitivity and specificity, Enzyme Linked Immunosorbent Assays (ELISA) were performed. All reagents were purchased from R&D Systems, Minnesota, MN, and four plates were developed according to the following protocols.

100 µL, 10 µg/mL of the appropriate capture antibody/conjugate solution (in PBS) was placed into the wells of a clear polystyrene microplate and the plate was sealed and incubated overnight at 4° C. The protein solution was discarded and the wells were washed with ~400 µL wash buffer (0.05% Tween 20 in PBS) 3 times before blocking the plates with 1% Bovine Serum Albumin in 10 mM PBS, pH 7.4, for 2 hours. The plates were washed 3 times again with wash buffer following blocking and were used the same day according to the following procedures.

100 µL of the sample antigen (2 ng/mL in PBS) was added to each well and the plate was gently tapped to ensure proper mixing before the plate was sealed and incubated at 25° C. for 2 hours. The wells were then washed as described above before addition of 100 µL of the biotinylated detection antibody (100 ng/mL for IL-12 and 200 ng/mL for TNF-α in PBS) and incubation for 2 hours at 25° C. Following the washing step, 100 µL Streptavidin-Horse Radish Peroxidase (1/200 dilution factor) was added to wells and the plate was incubated for 20 mins at 25° C. In addition to sealing the wells, the plate was covered with aluminum foil to avoid exposure to direct light. Finally, the plate was again washed and 100 µL substrate solution was added to the wells. The plate was sealed and covered with aluminum foil for 30 mins before stopping the reaction with 50 µL stop solution. The plate was tapped gently again to ensure thorough mixing and the optical intensity at 450 nm was determined using a Molecular Devices, Silicon Valley, Calif., SpectraMax M5 Plate Reader within 30 mins. The absorption due to bare plates at 540 and 570 nm were subtracted using the built-in wavelength correction of the instrument.

Tuning Electrochemical Impedance Spectroscopy Proof of Principle Gold disc electrodes (2 mm diameter) purchased from CH Instruments, Inc., Austin, Tex., were used throughout this study. Gold electrode was polished for 2 min with 1, 0.3 and 0.05 µm $Al_2O_3$ powder and was sonicated for 5 min in acetone, ethanol and DI water to remove alumina from the surface. Upon washing the electrode with copious amounts of DI water, cyclic voltammetry was performed on the bare gold electrode using a three electrode system (Au working electrode, Pt counter electrode and Ag/AgCl reference electrode) in a solution of 5 mM $[Fe(CN)_6]^{3-}/[Fe(CN)_6]^{4-}$, 0.1 M KCl and 10 mM PBS (pH=7.4) to obtain the formal potential and a peak-to-peak separation of ~60 mV (59 mV theoretical). Impedance measurements were taken subsequently from the electrode at the former potential obtained from cyclic voltammetry at a frequency range of 0.1 Hz to $10^5$ Hz, with amplitude of 5 mV. All electrochemical measurements were done with a CHI660C analyzer (CH Instruments Inc., Austin Tex., USA).

Immobilization of the antibodies onto the sensor surfaces was performed as previously reported (La Belle, J. T., Bhaysar, K., Svarovsky, S., Zhang, P., Bhavanandan, V., Sweeney, J., Alford, T., Wang, J., Joshi, L. 2007. A Cytokine Immunosensor Based Upon Label-Free Electrochemical Impedance Spectroscopy. Biosens. Bioelec. 23, 428-31). Briefly, self assembling layer of 16-mercaptohexadecanoic (16-MHDA) acid was formed on the previously cleaned gold electrode though thiol linkages. The electrodes were kept in MHDA solutions having a concentration of 1 mM to 25 mM (in absolute ethanol) for a period varying between 1 to 12 hr at room temperature. Most electrodes were immersed in 1 mM MHDA for 1 hr at RT since this setting was found to have a dense surface coverage while minimizing the background signal prior to further functionalization.

Carboxylate groups of MHDA were converted to succinimidyl esters by immersing the electrode in an aqueous solution of 40 mM 1-ethyl-3-(3-dimethylaminopropyl) carbodiimide (EDC) in the presence of 10 mM water soluble sulfo-derivative of N-hydroxysuccinimide (NHS) for 1 hr. After decanting the EDC-NHS and washing the sensor with DI water, the antibody (anti-IL-12 or anti-TNF-α) was then immobilized on the activated sensor surface by immersion into a 10 μg/mL solution (in PBS) of the desired antibody overnight at 4° C. The sensor was washed with PBS following immobilization and blocked by ethanolamine using an aqueous solution of 1% (w/v) for 30 minutes against non-specific binding, prior to antigen exposure at varying concentrations.

Electrochemical impedance spectroscopy was taken using a CHI660C Impedance Analyzer, gold disk working, platinum wire counter, and silver-silver chloride reference electrodes from 100 kHz to 1 Hz sweeps using a 250 mV DC offset and 5 mV AC potential. Initial testing was performed using bare gold working electrode and immobilized unconjugated and gold nanoparticle conjugated anti-IL-12 immobilized electrodes with 100 μL of 5 mM ferricyanaide-ferrocynaide redox probe in 1× phosphate buffered saline at pH 7.4. Concentration gradients of IL-12 were then made from 0 (buffer alone) to 10,000 μg/mL of target protein. Frequency analysis were used to show impedance at characteristic frequency for binding and plotted against concentration.

Results and Discussion

Figure 3:
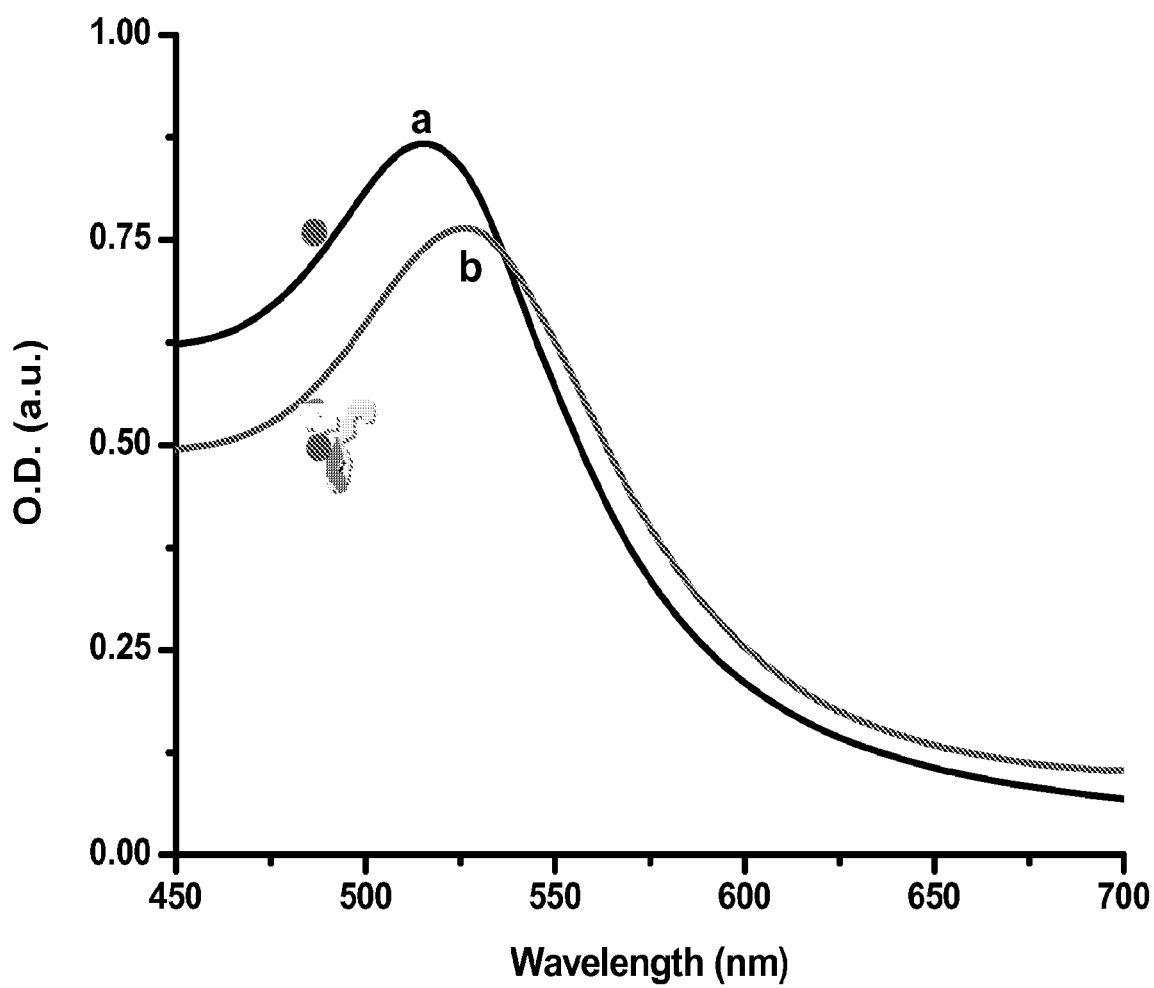
FIG. 3: UV-VIS absorbance spectra showing pre-conjugated spectra for AuNP (a) with peak at 516 nm and red shifted peak of AuNP conjugated mAb (b) with peak at 526 nm.

Gold Nanoparticle-Antibody Conjugation Conjugation of the AuNPs to a well established molecular recognition element, a monoclonal antibody (mAb), specifically anti-IL-12 was measured by pronounced Stokes (red) shift in thee UV-VIS absorbance spectra. The unconjugated AuNPs have a UV-VIS absorbance spectra with maximum peak at 516 nm (FIG. 3). Upon successful conjugation, a red shift to 526 nm is visible and expected (Shakila, V.; Pandian, K. Preparation of Gold Nanoislands on Various Functionalized Polymer-modified Glass and ITO for Electrochemical Characterization of Monolayer Assembly of Alkanethiols. 2007 J. Solid State Electrochem. 11, 296-302; Swift, J.; Butts, A.; Cheung-Lau, J.; Yerubandi, V.; Mochowski, I. J. Efficient Self-assembly of *Archaeoglobus fulgidus* Ferritin Around Metallic Cores. 2009 Langmuir 25, 5219-5225; Liu, Y.; Shipton, M. K.; Ryan, J.; Kaufman, E. D.; Franzen, S.; Feldheim, D. L. Synthesis, Stability, and Cellular Internalization of Gold Nanoparticles Containing Mixed Peptide-poly(ethylene glycol) Monolayers. 2007 Anal. Chem. 79, 2221-9). Separation between unconjugated and conjugated NPs is readily seen in this graph as well by observing the full width half maximum (FWHM). If the FWHM is greater, a mixture of unconjugated and conjugated NPs is present, but if the FWHM is same or slightly smaller, a high degree (purer) of separation has been accomplished as seen in the data.

Figures 4A, 4B:
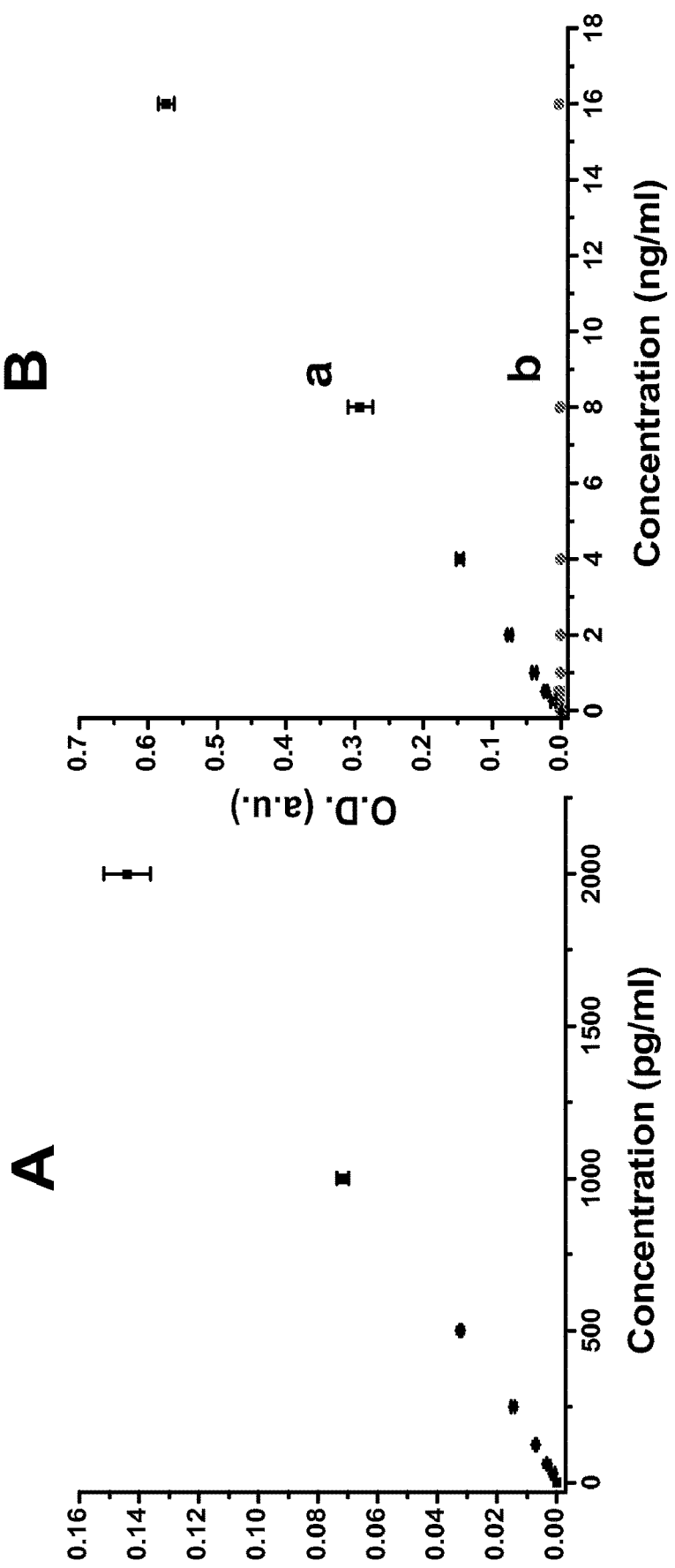
FIG. 4: ELISA verification of AuNP conjugated mAb functionality with "untuned" mAb function against IL-12 (A) compared to "tuned" conjugate (B) against IL-12 (a) and against TNF-a (b) showing high specificity remains for IL-12 and little to no cross reactivity to TNF-a.

Functional Verification of Gold Nanoparticle-Antibody Conjugates Successful conjugation is very important to the system but functionality of the conjugates is a must. To determine whether any ill effects occurred during conjugation, such as complete AuNP coverage of the antibody occurred, ELISA were performed. Firstly, the unconjugated anti-IL-12 was seeded on an ELISA plate and tested against IL-12 target to determine lower limits of detection (LDD) and responsivity as measured by the slope of the curve (FIG. 4A). The unconjugated anti-IL-12 bound IL-12 with a LLD of 3.9 pg/mL and a responsivity of $7.3 \times 10^{-4}$ (n=3, $R^2$=0.999). However, the AuNP conjugated anti-IL-12 (FIG. 4B, a), when tested against a concentration gradient, exhibited some decrease in LLD=60 pg/mL and responsivity=$3.6 \times 10^{-5}$ (n=3, $R^2$=0.999). To test against specificity, another protein, namely TNF-a, was run in the anti-IL-12 ELISA with minimal signal detection (FIG. 4B, b).

Figures 5A, 5B:
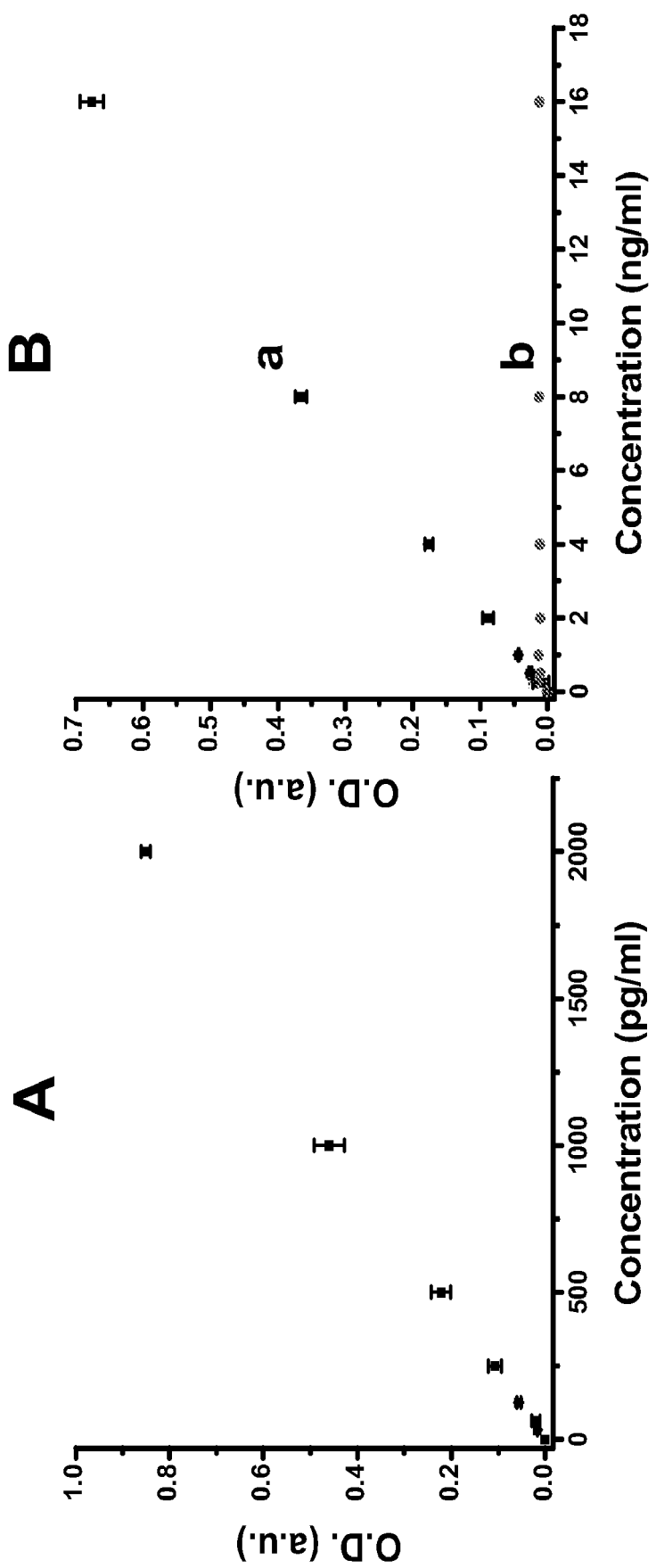
FIG. 5: ELISA verification of AuNP conjugated mAb functionality with "untuned" mAb function against TNF-a (A) compared to "tuned" conjugate (B) against TNF-a (a) and against IL-12 (b) showing high specificity remains for TNF-a and little to no cross reactivity to IL-12.

The results from the TNF-α ELISA were similar in trends. The unconjugated anti-TNF-α:TNF-α results (FIG. 5A) had an LLD of 3.4 pg/mL and responsivity=$4.3 \times 10^{-4}$ (n=3, $R^2$=0.999) and when conjugated (FIG. 5B, a), the system's LLD went to 109 pg/mL with responsivity=$4.3 \times 10^{-5}$ (n=3, $R^2$=0.999). Again, there was little to no cross reactivity when presented with the other marker, IL-12 in this case (FIG. 5B, b).

Figures 6A, 6B:
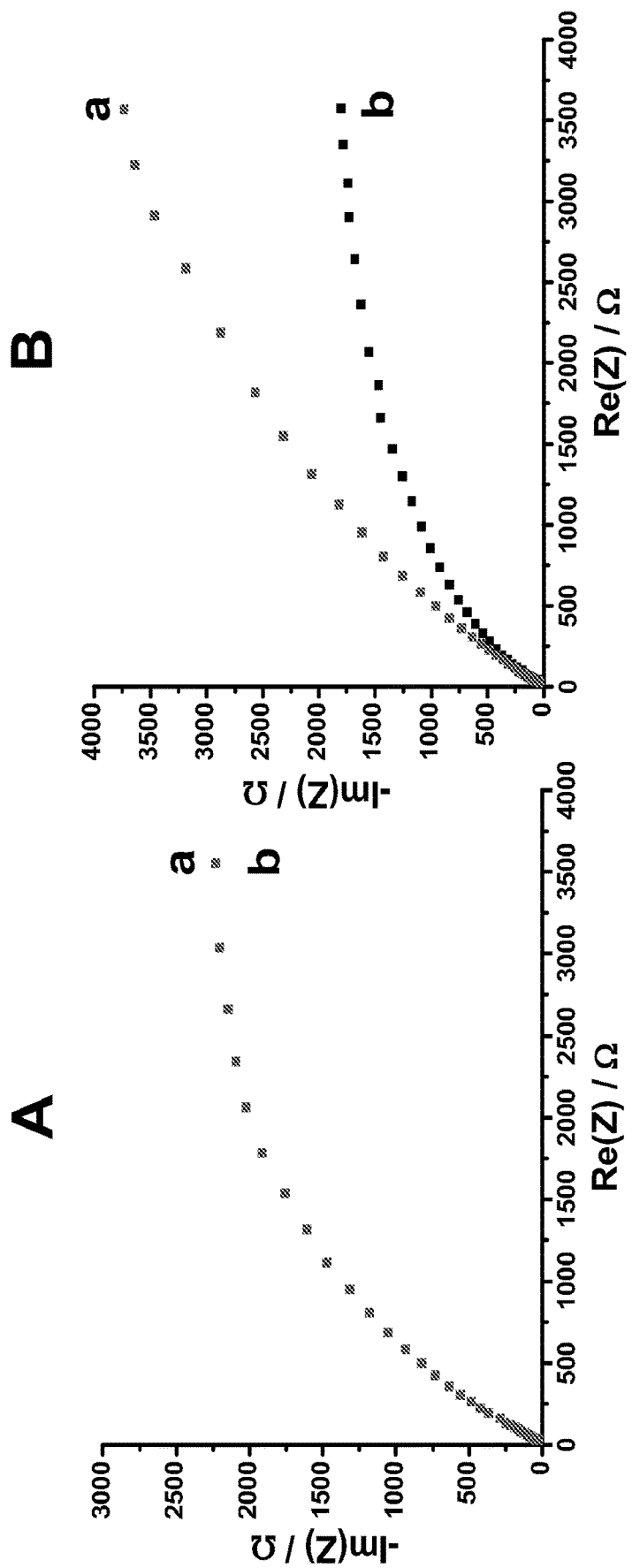
FIG. 6: (A) Nyquist responses (a) immobilized unconjugated antibodies and (b) bare electrodes (with no linker or antibody). Nyquist responses (B) for electrodes with conjugated antibodies immobilized on them (a) and with no AuNPs conjugated on them (b). Note: all sensors were run "bare" prior to antibody or antibody-AuNP conjugates were attached to them.

Tuning Electrochemical Impedance Spectroscopy Proof of Principle The initial testing performed included a comparison between two sets of sensors (n=4 total) with two sensors with unconjugated anti-IL-12 immobilized (FIG. 6A a) compared to the sensors Nyquist prior to immobilization (FIG. 6A b) showing little or slight change in impedance indicating successful immobilization but no altered or adjusted impedance. However, once the immobilization of an AuNP conjugated anti-IL-12 sensor was run, the Nyquist exhibited a marked change in impedance (FIG. 6B a) as compared to the reading prior to immobilization (FIG. 6B, b) indicating a significant change in impedance has occurred.

Figures 7A, 7B:
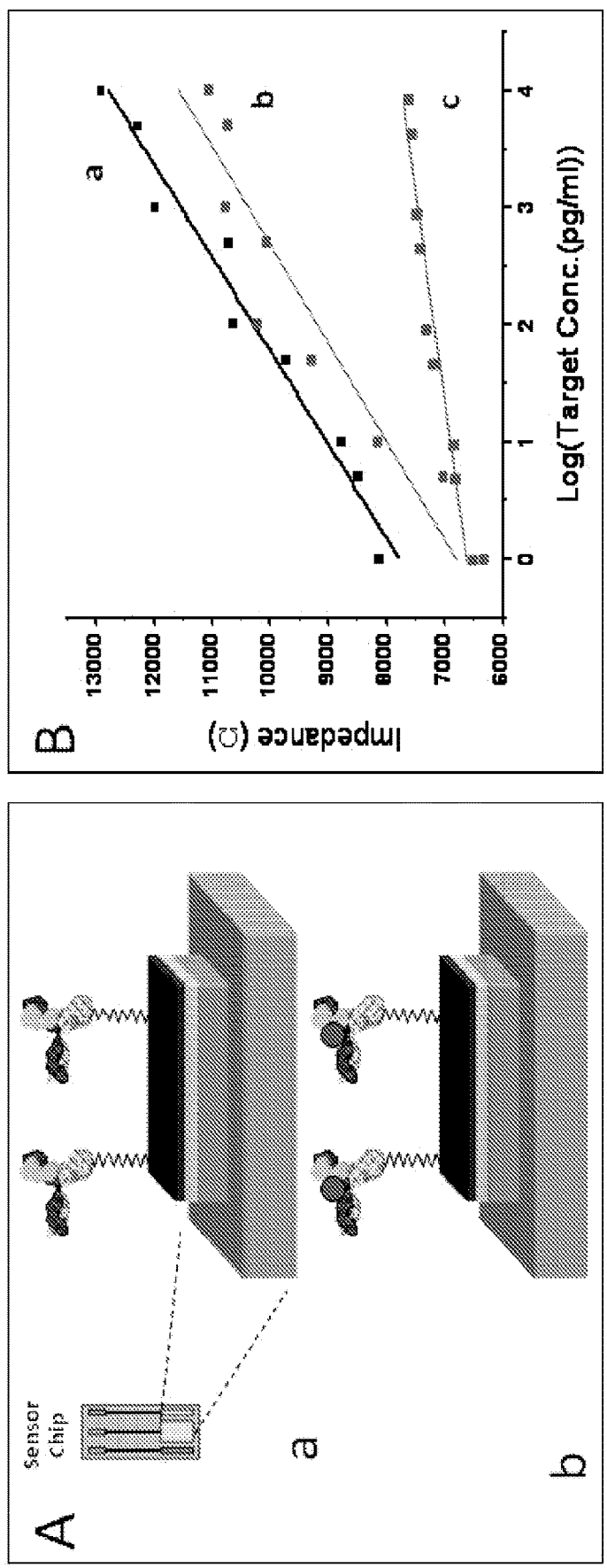
FIG. 7: Schematics for (A) "untuned" (a) and AuNP "tuned" (b) mAb with results demonstrating feasibility (B) with "untuned" anti-IL-12:IL-12 binding showing typical 5 Hz optimal response (a) to "tuned" response now shifted to 1 Hz (b) as well as verification of reduced 5 Hz response for the "tuned" system back at 5 Hz (c).

To determine the exact nature of this change, and to see if a successful tuning occurred, a concentration gradient of IL-12 was run again the unconjugated (FIG. 7 A, a) and conjugated sensors (FIG. 7 A, b). When the concentration gradient was run against the unconjugated antibody sensor, a typical 5 Hz signal was seen (FIG. 7B, a). However, in the case of the conjugated (or tuned), the maximal response was detected at 1 Hz (FIG. 7B, b), 4 Hz away from typical response. Verifying that the 5 Hz signal is no longer an optimal frequency on this "tuned" sensor shows that little signal is measureable over 4 log orders of concentration (FIG. 7B, c). This albeit slight shift of 4 Hz was performed using a 10 nm AuNP. However, if a smaller particle or different material besides gold could be used, the electrical properties of the system might be adjusted much more such that more than 10 Hz signal shifting could be possible. In the case of two targets being close to one another, one type of tuning element could shift the lower frequency even lower while the other tuning element could shift the higher one higher, thereby optimizing the two to be the furthest away from one another as possible. Most biomarkers tend to have frequencies associated with them at or below 1 kHz, with plenty of room for at least five biomarkers to be tuned significantly apart in this region.

In this example, the inventors have demonstrated a tuning of the electrochemical impedance spectra frequency element for the potential of multiplexing multiple markers onto a single sensor. By use of a 10 nm diameter gold colloidal nanoparticle, slight tuning was obtained, albeit only 4 Hz with a model inflammatory disease marker. The inventors also have demonstrated the tuning using 5 nm and 20 nm diameter sizes of AuNs. By conjugation of the NP to the molecular recognition element rather than the target, timely and complicated labeling (of the target) steps were avoided. With this principle, extension of the tuning to 10's to 100's of Hz should be made possible by designing a better conjugation, that is, use of alternative sizes, materials, and perhaps particle to molecular recognition element spacing.

With this strategy in mind, markers such as glucose, insulin, CRP, IL-2RA, and HbA1c can now be incorporated into a single test strip that could be use to more accurately monitor diabetes management. The frequency can be changed by using different sized particles, different materials, and different length of spacer between the particles and the molecular recognition elements. Optimization of these features will allow optimization of the model with specific markers for diabetes and other diseases as recommended by the community and literature. Using EIS to determine the interaction between such disease biomarkers and their corresponding molecular recognition elements optimal frequencies designing the tuning required, incorporating all elements onto a single sensor is now possible.

Example—Stress Monitoring System

Figure 11:
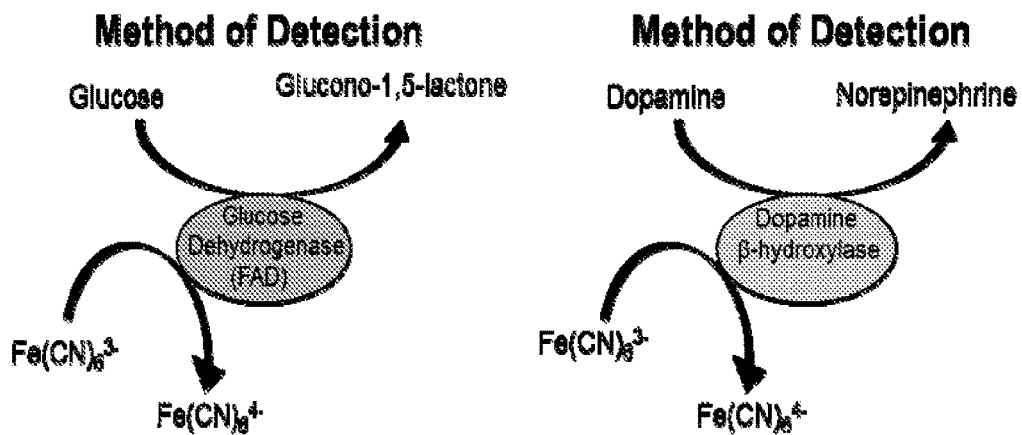
FIG. 11: Method of detection using an enzyme which in turn produces a measurable current.

Catecholamines are typically synthesized in a cascade fashion (FIG. 11), the enzymes that are used to synthesize the catecholamines could also be used to develop an enzymatic electrochemical sensor much akin to blood glucose sensing. In this case however, the sensor could be placed subcutaneously inside a needle in the patient's arm, leg, waist, etc. In the finalized version, a wireless system of data transfer would allow for the sensor to transmit to a data logger for later analysis (in the case of a pilot flying a mission) or perhaps wireless to a command module where the data could be monitored in real-time (in the case of firefighters, for example).

Taking just one of these markers, e.g., epinephrine, a catecholamine, it can be observed in blood (plasma) at normal (resting) levels of 2.7 nM. However, simply moving to the supine position and within 30 min, the levels are <273 pM, or sitting <328 pM or standing (30 min)<4.9 nM. However, in conditions of extreme stress, these levels can change to >26.7 nM. The amount of change and the direction (increase or decrease) depends upon the type of stress (here defined as from dehydration, to fatigue, to shock, to trauma, or extreme activity). However, to only use this one indicator would make it quite difficult to differentiate the degree of stress a person is under or which type. To further (correctly) indentify the type of stress, one only has to look at this indicator amongst others (Table 1).

| Glucose | Norepinephrine | Lactate | physiological condition |
| --- | --- | --- | --- |
| baseline | baseline | baseline | normal |
| lowered | lowered | elevated | shock |
| lowered | elevated | lowered | fatigue |
| lowered | elevated | elevated | extreme fatigue |
| elevated | lowered | lowered | trauma |
| elevated | elevated | lowered | extreme trauma |
| elevated | elevated | elevated | extreme physical activity |

The development of a convenient, continuous time STRESS monitoring system for measurements of multiple stress markers has the potential for providing instantaneous feedback at critical moments or in extreme environments. The present example provides benchmark studies to show efficacy of such a monitoring technique.

Figure 12:
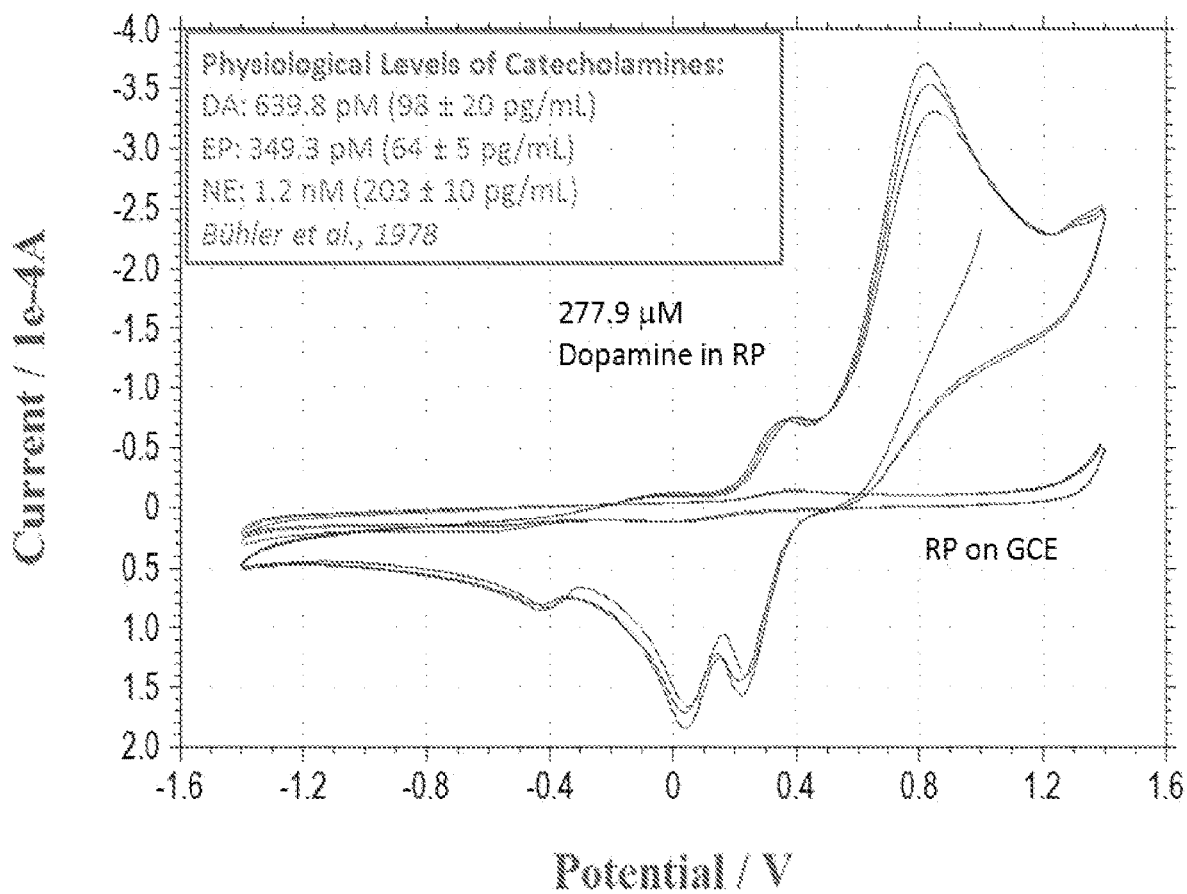
FIG. 12: Cyclic voltammetry (CV) of 277.9 mM Dopamine in 100 mM ferri, 100 mM ferrocyanide (Redox Probe or RP) on Glassy Carbon Electrode (GCE).

Catecholamines are electro-active biomarkers that can be monitored electrochemically. Preliminary benchmark testing has shown that Catecholamines generate measurable responses when using electrochemical techniques. The levels of the Catecholamines can be accessed using electrochemical techniques like cyclic and square wave voltammetry either in purified or mixed forms. FIG. 12 shows a cyclic voltammogram for Dopamine (blue line) compared to that of a standard redox probe electro-active solution (red line). This testing verified that there is a sufficient background for differentiating between the Catecholamines using electrochemical means.

Figure 13:
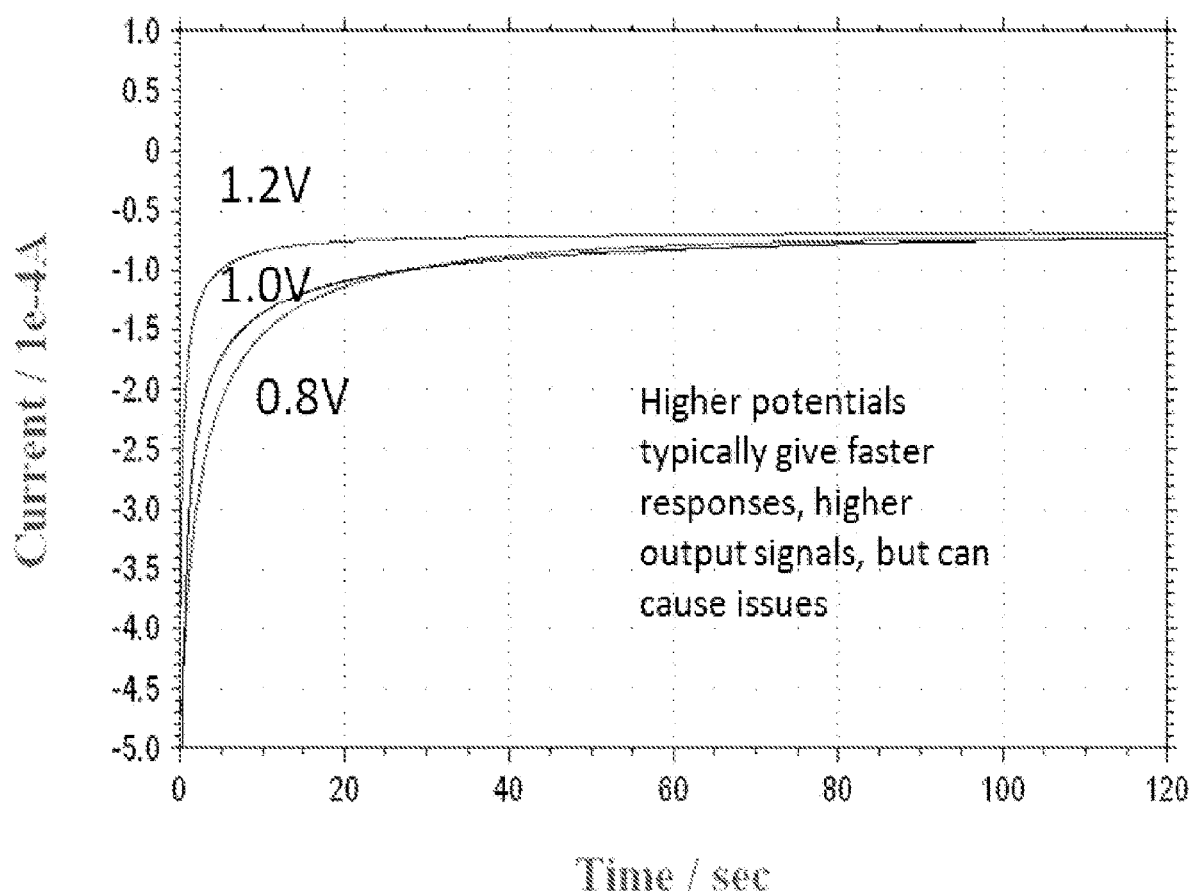
FIG. 13: 277.9 mM (98 mg/mL) Dopamine in RP on GCE.
Figure 14:
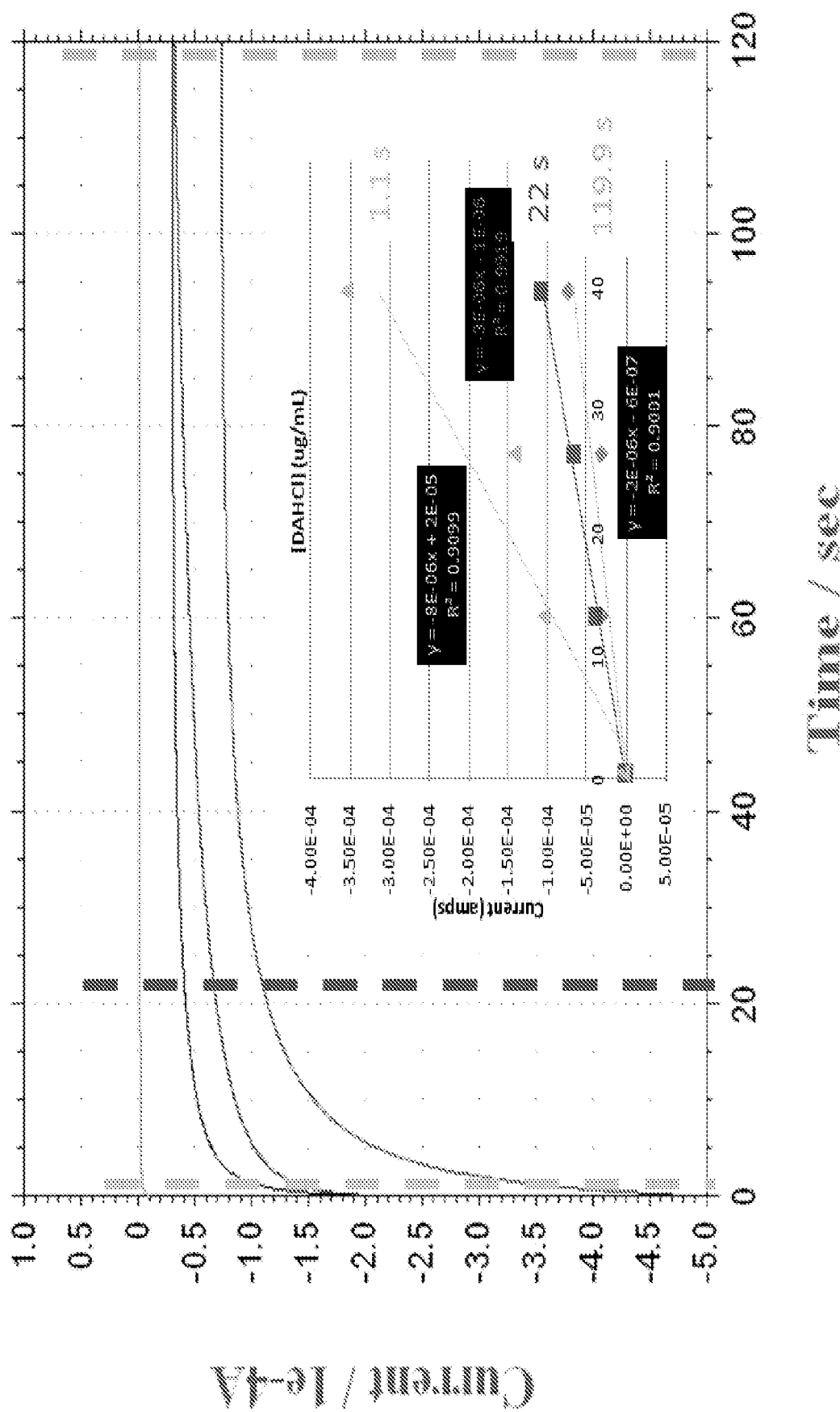
FIG. 14: 0.8 V applied, dopamine in RP starting at 227.9 mM (98 mg/mL).
Figure 15:
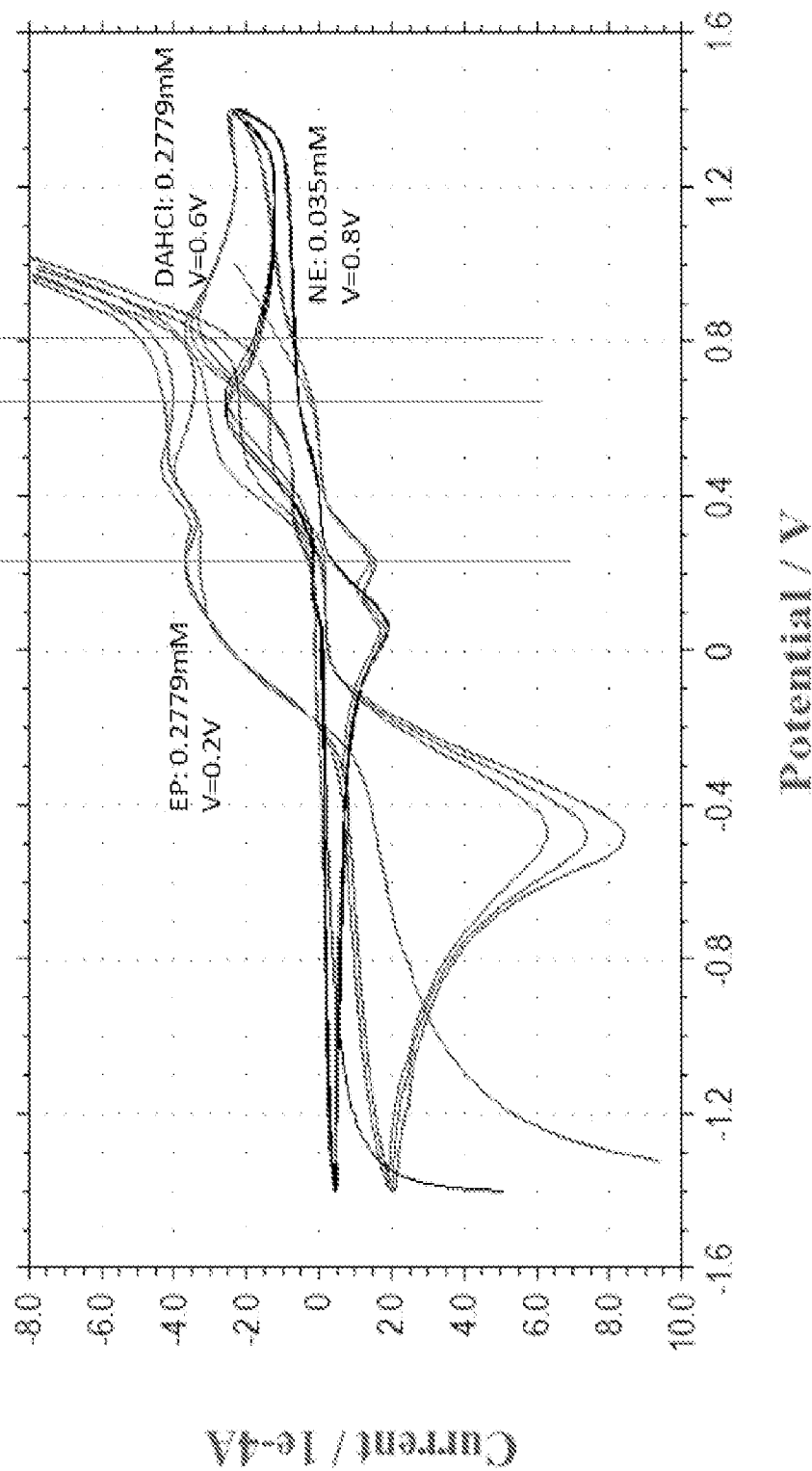
FIG. 15: Overlays of Catecholamines—problem with single sensor design

Additional preliminary bench-top studies have uncovered a potential problem with monitoring several Catecholamines using a single sensor. As can be observed in FIG. 13, higher potentials were found to give faster responses using Dopamine. This is further shown by the response times of Dopamine concentration in FIG. 14. While the faster responses are advantageous for sensing purposes, it also presents challenges. In particular, as shown in the overlay plot in FIG. 15, Dopamine, Epinephrine, and Norepinephrine each showed similar response peaks at higher potentials between 0.6-1.0 Volts. This would present a challenge in clearly differentiating between which Catecholamine was detected due to the lack of baseline between each of the other Catecholamines being monitored. A desired response can be observed in FIG. 15 with the first peak of Epinephrine recorded between 0.2-0.3 Volts. The occurrence of this peak was clearly separated from the responses of Dopamine and Norepinephrine recorded at the same potential. Because the Catecholamines show similar response behaviors over a wide range of high potentials (and conversely not sufficient separation at specific lower potentials), a sensor system could be implemented instead of a single sensor design. This would keep the desired fast response time while also allowing for clear differentiation of the Catecholamines.

Figure 16:
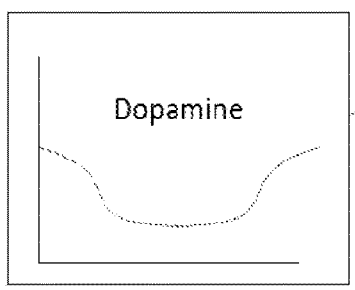
FIG. 16: Overlays of Catecholamines—organization of the individual sensors as worn by an individual.
Figure 16:
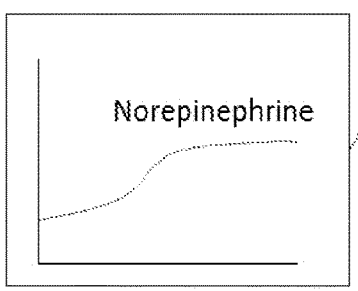
Figure 16:
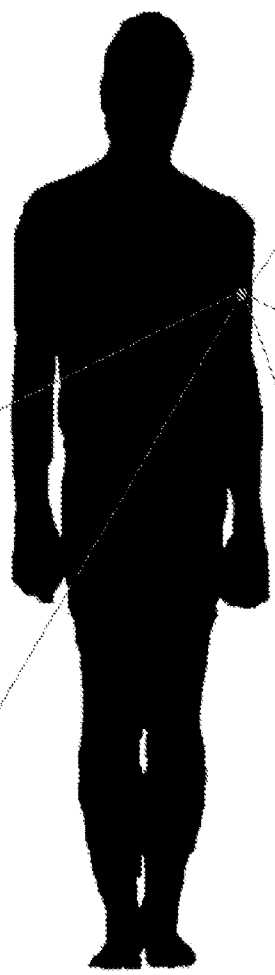
Figure 16:
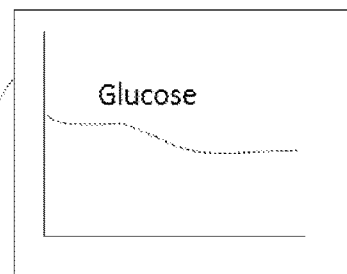
Figure 16:
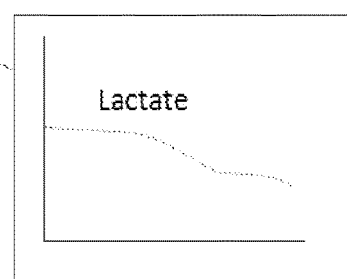
Figure 16:
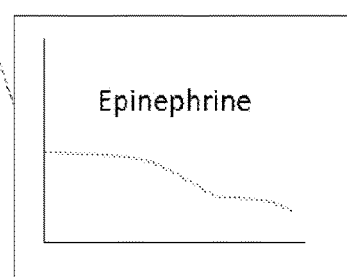
Figure 17:
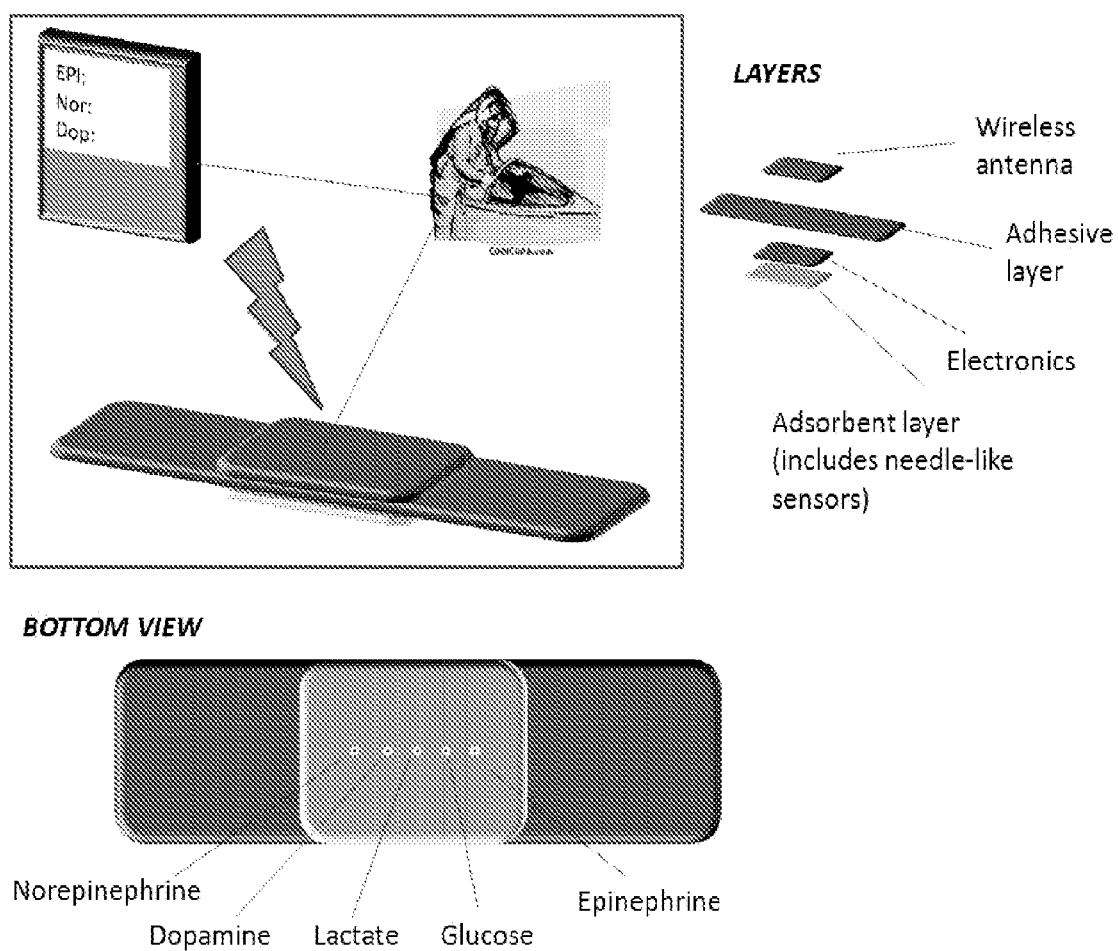
FIG. 17: Overlays of Catecholamines—design of stress sensors. The needle-like sensors would be connected to electronics within the patch for data acquisition and could be wirelessly transmitted for instantaneous monitoring of Catecholamine, lactate, and glucose levels.

The sensor system would include individual sensors for each of the different Catecholamines, as well as lactate and glucose, arranged on a wearable patch. As can be seen in FIG. 16, the individual sensors themselves would be organized on an adsorbent layer that would weakly puncture the skin when worn. The needle-like sensors would be connected to electronics within the patch for data acquisition and could be wirelessly transmitted for instantaneous monitoring of Catecholamine, lactate, and glucose levels (FIG. 17). After successful sensing of Catecholamines, glucose, and lactate, the sensor design can modified to incorporate monitoring for pH, EKG, hydration, pO2 and pCO2 levels.

The invention claimed is:

1. A multi-marker electrochemical impedance spectroscopy sensor configured for simultaneous detection of multiple distinct unlabeled target agents, the sensor comprising multiple distinct molecular recognition elements disposed on a single electrode;
   wherein each molecular recognition element is distinctly sensitive to a corresponding unlabeled target agent, each molecular recognition element comprising a distinct binding partner of the corresponding unlabeled target agent and conjugated to a corresponding tuning element that is specific to said molecular recognition element;
   wherein, when each unlabeled target agent becomes a bound target agent by binding to the molecular recognition agent corresponding to that unlabeled target agent, the presence of the corresponding tuning element on said molecular recognition element alters the electrochemical impedance behavior of said molecular recognition element such that a characteristic feature of the electrical impedance spectrum of each different bound target agent is distinguishable from one or more characteristic features of the electrical impedance spectrum of any other of the different bound target agents on said sensor, thereby providing simultaneous detection of the different bound target agents.

2. The sensor of claim 1 wherein said molecular recognition elements are independently selected from the group consisting of antibodies, enzymes, receptors, ligands, antigens, DNA, RNA, peptides, and synthetic antibodies.

3. The sensor of claim 1, wherein all of the molecular recognition elements are either all antibodies, all enzymes, all receptors; or all ligands.

4. The sensor of claim 1, wherein the molecular recognition elements disposed on the single electrode are a mixture of antibodies, enzymes, receptors, and ligands.

5. The sensor of claim 1, wherein each tuning element is selected from the group consisting of magnetic nanobeads, polystyrene beads, carbon nanotubes, nanowires, nanocolloids, nanoparticles, nanorods, quantum dots, nanocrystals, liposomes, silica beads, latex beads, and gold colloids.

6. The sensor of claim 1, wherein the tuning element corresponding to each molecular recognition element is directly affixed to said molecular recognition element.

7. The sensor of claim 1, wherein the tuning element corresponding to each molecular recognition element is affixed to said molecular recognition element through a peptide linker or physical adsorption.

8. The sensor of claim 1, wherein the tuning element corresponding to each molecular recognition element is a nanoparticle of 2-20 nm in diameter.

9. The sensor of claim 1, wherein the tuning element corresponding to each molecular recognition element is affixed to said molecular recognition element through a functional group on said label wherein said functional group is selected from the group consisting of biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin and biotin binding proteins.

10. The sensor of claim 1, wherein each molecular recognition element is affixed to said sensor surface through a linkage with the tuning element corresponding to said molecular recognition element; and wherein the tuning element corresponding to each molecular recognition element is affixed to said sensor surface through a functional group corresponding to that tuning element.

11. The sensor of claim 9, wherein the functional group affixing said tuning element to said sensor surface is selected from the group consisting of biotin, hydrazine, alkynyl, alkylazide, amino, hydroxyl, thiol, aldehyde, phosphoinothioester, maleimidyl, succinyl, succinimidyl, isocynate, ester, strepavidin, avidin, neuavidin and biotin binding proteins.

12. A method of determining the presence of a plurality of biomarkers in a biological sample, comprising:
    a. contacting the sample with the sensor of claim 1,
    b. measuring the frequency-dependent electrical impedance of the sensor to produce an impedance spectrum measurement; and
    c. identifying, for each biomarker of the plurality of biomarkers, one or more features of the impedance spectrum attributable to that biomarker.

13. The method of claim 12, wherein said impedance spectrum measurement is obtained by applying a time-varying voltage to the single electrode of the sensor, the time-varying input voltage having an AC amplitude of 5 mV, a DC offset of 250 mV, and varying a frequency of the input voltage from 0.1 Hz to $10^5$ Hz.

\* \* \* \* \*